(12) United States Patent
Shih et al.

(10) Patent No.: US 7,183,320 B2
(45) Date of Patent: Feb. 27, 2007

(54) BENZOYLSULFONAMIDES AND SULFONYLBENZAMIDINES FOR USE AS ANTITUMOUR AGENTS

(75) Inventors: Chuan Shih, Carmel, IN (US); Cora Sue Grossman, Indianapolis, IN (US); Karen Lynn Lobb, Indianapolis, IN (US); Thomas Hughes Corbett, Gross Pointe Park, MI (US); Ho-Shen Lin, Indianapolis, IN (US); Philip Arthur Hipskind, New Palestine, IN (US)

(73) Assignee: Eli Lilly and Company, Indianapolis, IN (US)

(*) Notice: Subject to any disclaimer, the term of this patent is extended or adjusted under 35 U.S.C. 154(b) by 349 days.

(21) Appl. No.: 10/478,389

(22) PCT Filed: May 24, 2002

(86) PCT No.: PCT/US02/15142

§ 371 (c)(1),
(2), (4) Date: Nov. 18, 2003

(87) PCT Pub. No.: WO02/098848

PCT Pub. Date: Dec. 12, 2002

(65) Prior Publication Data

US 2004/0157741 A1    Aug. 12, 2004

(51) Int. Cl.
*A61K 31/165*    (2006.01)
*C07C 303/00*    (2006.01)
(52) U.S. Cl. .................................. 514/617; 564/91
(58) Field of Classification Search ............. 564/91; 514/617
See application file for complete search history.

(56) References Cited

U.S. PATENT DOCUMENTS

| | | | | |
|---|---|---|---|---|
| 4,157,257 A | | 6/1979 | Takematsu et al. | |
| 4,233,061 A | | 11/1980 | Takematsu et al. | |
| 4,266,078 A | * | 5/1981 | Pallos ........................ | 564/91 |
| 4,347,380 A | * | 8/1982 | Pallos ........................ | 564/91 |
| 4,433,997 A | * | 2/1984 | Pallos ........................ | 504/104 |
| 4,495,365 A | * | 1/1985 | Pallos ........................ | 564/91 |
| 4,845,128 A | * | 7/1989 | Harper et al. .............. | 514/592 |
| 5,110,830 A | * | 5/1992 | Harper et al. .............. | 514/592 |
| 5,929,097 A | | 7/1999 | Du et al. | |
| 6,380,167 B1 | * | 4/2002 | Braude ....................... | 514/26 |
| 2002/0055631 A1 | | 5/2002 | Augeri et al. | |
| 2002/0086887 A1 | | 7/2002 | Augeri et al. | |

FOREIGN PATENT DOCUMENTS

| | | |
|---|---|---|
| DE | 27 44 137 | 4/1978 |
| EP | 0 602 878 A1 | 6/1994 |
| EP | 0 927 716 A | 7/1999 |
| WO | WO 02/24636 | 3/2002 |

OTHER PUBLICATIONS

Yoneyama, K. Phytotoxic Activity of N-Phenylsulfonylbenzamides, Oct. 6, 1982, Agric. Biol. Chem., vol. 47, Issue 3, pp. 593-596, especially p. 594.*

Greenridge, P.A., et al., "Pharmacophores incorporating numerous excluded volumes defined by x-ray crystallographic structure in three-dimensional database searching: application to the thyroid hormone receptor;" 1998, J. Med. Chem., vol. 41, No. 14, pp. 2503-2512.

* cited by examiner

*Primary Examiner*—Joseph K. McKane
*Assistant Examiner*—Susannah L. Chung
(74) *Attorney, Agent, or Firm*—Tina M. Tucker; Robert Titus

(57) ABSTRACT

The present invention provides antitumor compounds of the formula (I), and antitumor methods (I)

11 Claims, No Drawings

BENZOYLSULFONAMIDES AND SULFONYLBENZAMIDINES FOR USE AS ANTITUMOUR AGENTS

BACKGROUND OF THE INVENTION

In recent years fundamental advances have been made in the development of chemical agents and regimens of therapy to combat neoplastic diseases. Despite these continuing advances, cancers continue to exact intolerable levels of human pain and suffering. The need for new and better methods of treating malignant neoplasms and leukemias continues to fuel efforts to create new classes of compounds, especially in the area of inoperable or metastatic solid tumors. The recent avalanche of information regarding the basic biological processes involved in neoplasms has led to a deeper understanding of the heterogeneity of tumors. It is because of this extreme heterogeneity among populations of neoplastic cells that new chemotherapeutic agents should have a wide spectrum of activity and an acceptable therapeutic index. In addition, such agents must be chemically stable and compatible with other agents. It is also important that any chemotherapeutic regimen be as convenient and painless as possible to the patient.

Chemotherapy and radiation are frequently used in the treatment of cancer and, although they often produce some response in the malignant disease, they are rarely curative. Most solid tumors increase in mass through the proliferation of malignant cells and stromal cells, including endothelial cells. In order for a tumor to grow larger than 2–3 millimeters in diameter, it must form a vasculature, a process known as angiogenesis. Suppression of tumor-induced angiogenesis by angiostatin and endostatin has been reported to result in antitumor activity (O'Reilly, et al., *Cell*, 88, 277–285 (1997)). Because angiogenesis is a critical component of the mass expansion of most solid tumors, the development of new agents for the inhibition of this process represents a promising approach for antitumor therapy. This approach to antitumor therapy may lack the toxic side effects or drug resistance-inducing properties of conventional chemotherapy (Judah Folkman, *Endoggnous Inhibitors of Angiogenesis*, The Harvey Lectures, Series 92, pages 65–82, Wiley-Liss Inc., (1998)).

The N-[benzoyl]-phenylsulfonamides are well known in the agricultural chemical arts as insecticides and herbicides (DE 2744137). The use of N-[benzoyl]-phenylsulfonamides as antitumor agents generally, or as inhibitors of angiogenesis specifically, were heretofore not appreciated.

BRIEF SUMMARY OF THE INVENTION

The present invention provides a compound of Formula I:

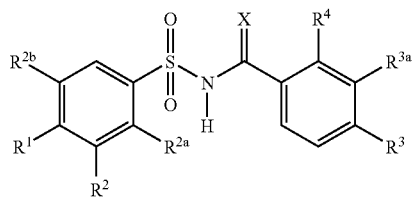

where:
X is O or NH;
$R^1$ is hydrogen, halo, $C_1$–$C_6$ alkyl, $C_1$–$C_4$ alkoxy, $C_1$–$C_4$ alkylthio, $CF_3$, $OCF_3$, $SCF_3$, ($C_1$–$C_4$ alkoxy)carbonyl, nitro, azido, $O(SO_2)CH_3$, $N(CH_3)_2$, hydroxy, phenyl, substituted phenyl, pyridinyl, thienyl, furyl, quinolinyl, or triazolyl;
$R^2$ is hydrogen, halo, cyano, $CF_3$, $C_1$–$C_6$ alkyl, ($C_1$–$C_4$ alkoxy)carbonyl, $C_1$–$C_4$ alkoxy, phenyl, or quinolinyl;
$R^{2a}$ is hydrogen or $C_1$–$C_4$ alkoxy;
$R^{2b}$ is hydrogen or $C_1$–$C_6$ alkyl provided that at least one of $R^{2a}$ and $R^{2b}$ is hydrogen;
$R^3$ is hydrogen, halo, $C_1$–$C_6$ alkyl, $CF_3$, or nitro;
$R^{3a}$ is hydrogen, halo, or $C_1$–$C_6$ alkyl provided that when $R^{3a}$ is $C_1$–$C_6$ alkyl, $R^3$ is hydrogen and $R^4$ is halo; and
$R^4$ is halo, $C_1$–$C_6$ alkyl, or $CF_3$ provided that only one of $R^3$ and $R^4$ may be $C_1$–$C_6$ alkyl and provided that when $R^4$ is halo or $C_1$–$C_6$ alkyl only one of $R^3$ and $R^{3a}$ is hydrogen; or a pharmaceutically acceptable base addition salt thereof, provided that:
a) when $R^3$ and $R^4$ are both chloro and $R^2$ is hydrogen, $R^1$ is bromo, iodo, $C_1$–$C_4$ alkoxy, $C_1$–$C_4$ alkylthio, $CF_3$, $OCF_3$, nitro, azido, $O(SO_2)CH_3$, $N(CH_3)_2$, hydroxy, phenyl, substituted phenyl, pyridinyl, thienyl, furyl, or triazolyl;
b) when $R^3$ and $R^4$ are both chloro and $R^1$ is hydrogen, $R^2$ is bromo, fluoro, $CF_3$, $C_1$–$C_6$ alkyl, $C_1$–$C_4$ alkoxy, phenyl, or quinolinyl.

The present invention further provides a method of treating susceptible neoplasms in a mammal comprising administering to a mammal in need of such treatment an oncolytically effective amount of a compound of Formula II:

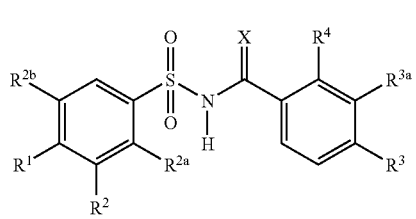

where:
X is O or NH;
$R^1$ is hydrogen, halo, $C_1$–$C_6$ alkyl, $C_1$–$C_4$ alkoxy, $C_1$–$C_4$ alkylthio, $CF_3$, $OCF_3$, $SCF_3$, ($C_1$–$C_4$ alkoxy)carbonyl, nitro, azido, $O(SO_2)CH_3$, $N(CH_3)_2$, hydroxy, phenyl, substituted phenyl, pyridinyl, thienyl, furyl, quinolinyl, or triazolyl;
$R^2$ is hydrogen, halo, cyano, $CF_3$, $C_1$–$C_6$ alkyl, ($C_1$–$C_4$ alkoxy)carbonyl, $C_1$–$C_4$ alkoxy, phenyl, or quinolinyl;
$R^{2a}$ is hydrogen or $C_1$–$C_4$ alkoxy;
$R^{2b}$ is hydrogen or $C_1$–$C_6$ alkyl provided that at least one of $R^{2a}$ and $R^{2b}$ is hydrogen;
$R^3$ is hydrogen, halo, $C_1$–$C_6$ alkyl, $CF_3$, or nitro;
$R^{3a}$ is hydrogen, halo, or $C_1$–$C_6$ alkyl provided that when $R^{3a}$ is $C_1$–$C_6$ alkyl, $R^3$ is hydrogen and $R^4$ is halo; and
$R^4$ is halo, $C_1$–$C_6$ alkyl, or $CF_3$ provided that only one of $R^3$ and $R^4$ may be $C_1$–$C_6$ alkyl and provided that when $R^4$ is halo or $C_1$–$C_6$ alkyl only one of $R^3$ and $R^{3a}$ is hydrogen; or a pharmaceutically acceptable base addition salt thereof.

The present invention also provides a method of suppressing tumor angiogenesis in a mammal comprising administering to a mammal in need of such treatment an angiogenesis suppressing amount of a compound of Formula II or a pharmaceutically acceptable base addition salt thereof.

The present invention also provides a pharmaceutical formulation comprising a compound of Formula II or a pharmaceutically acceptable base addition salt thereof, in combination with a pharmaceutically acceptable carrier, diluent or excipient.

This invention also provides the use of a compound of Formula II for the manufacture of a medicament for the treatment of susceptible neoplasms. Additionally, this invention provides a pharmaceutical formulation adapted for the treatment of susceptible neoplasms containing a compound of Formula II. Furthermore, this invention includes a method for the treatment of susceptible neoplasms that comprises administering an effective amount of a compound of Formula II.

DETAILED DESCRIPTION OF THE INVENTION

The general chemical terms used in the formulae above have their usual meanings. For example, the term "$C_1$–$C_6$ alkyl" includes methyl, ethyl, propyl, isopropyl, butyl, isobutyl, sec-butyl, tert-butyl, pentyl, and hexyl moieties. The term "$C_1$–$C_4$ alkyl" is included within the meaning of $C_1$–$C_6$ alkyl and is taken to mean methyl, ethyl, propyl, isopropyl, butyl, isobutyl, sec-butyl, and tert-butyl. The term "$C_1$–$C_4$ alkoxy" is taken to mean a $C_1$–$C_4$ alkyl group linked to the parent molecule through an oxygen atom, and includes the groups methoxy, ethoxy, and isopropoxy. Likewise, the term "$C_1$–$C_4$ alkylthio" is taken to mean a $C_1$–$C_4$ alkyl group linked to the parent molecule through a sulfur atom, and includes methylthio, ethylthio, and isobutylthio. The term "halo" is taken to mean chloro, fluoro, bromo, and iodo. The term "substituted phenyl" means a mono-substituted phenyl wherein the substitutions are selected from the group consisting of $C_1$–$C_4$ alkoxy, $C_1$–$C_4$ alkylthio, $C_1$–$C_4$ acyl, trifluoromethyl, and halo. The term "acyl" refers to an organic acid group in which the OH of the carboxy group is replaced by some other substituent (RCO—).

When X=NH, the molecule can exist in two tautomeric forms,

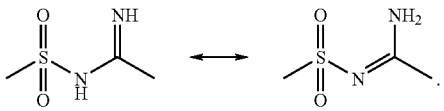

The present invention contemplates both of these forms.

While all of the compounds of Formula II are useful antitumor agents, certain classes of compounds are preferred. The following paragraphs describe such preferred classes.

a) $R^1$ is hydrogen and $R^2$ is bromo;
b) $R^1$ is fluoro and $R^2$ is chloro;
c) $R^1$ is fluoro;
d) $R^1$ is chloro;
e) $R^1$ is methyl;
f) $R^1$ is methylthio;
g) $R^2$ is hydrogen;
h) $R^3$ is chloro, bromo, or $CF_3$;
i) $R^3$ is chloro;
j) $R^3$ is bromo;
k) $R^3$ is $CF_3$;
l) $R^{1a}$ is hydrogen;
m) $R^4$ is chloro, bromo, methyl, or $CF_3$;
n) $R^4$ is chloro;
o) $R^4$ is bromo;
p) $R^4$ is methyl;
q) $R^4$ is $CF_3$;
r) $R^3$ and $R^4$ are both chloro;
s) $R^3$ and $R^4$ are both $CF_3$;
t) $R^3$ is bromo and $R^4$ is chloro;
u) $R^{3a}$ is hydrogen and $R^3$ and $R^4$ are other than hydrogen;
v) X is O;
w) The compound of Formula II wherein the compound is a pharmaceutically acceptable base addition salt;
x) The compound of Formula II wherein the compound is a sodium salt;
y) $R^1$, $R^{2a}$, and $R^{2b}$ are hydrogen and $R^2$ is selected from the group consisting of halo, $C_1$–$C_4$ alkyl, $C_1$–$C_4$ alkoxy, cyano, trifluoromethyl, and quinolinyl;
z) $R^2$ and $R^{2b}$ are hydrogen, $R^1$ is halo or $C_1$–$C_4$ alkyl, and $R^{2a}$ is $C_1$–$C_4$ alkyl or $C_1$–$C_4$ alkoxy; or
aa) $R^{2a}$ is hydrogen, $R^1$ is $C_1$–$C_4$ alkoxy, and $R^2$ and $R^{2b}$ are $C_1$–$C_4$ alkyl.

Additionally, the following classes are especially preferred.

a) $R^2$, $R^{2a}$, and $R^{2b}$ are hydrogen and $R^1$ is selected from the group consisting of hydrogen, halo, $C_1$–$C_6$ alkyl, $C_1$–$C_4$ alkoxy, $C_1$–$C_4$ alkylthio, $CF_3$, $OCF_3$, $SCF_3$, ($C_1$–$C_4$ alkoxy)carbonyl, nitro, azido, $O(SO_2)CH_3$, $N(CH_3)_2$, hydroxy, phenyl, substituted phenyl, pyridinyl, thienyl, furyl, quinolinyl, and triazolyl; or
b) $R^{2a}$ and $R^{2b}$ are hydrogen and $R^1$ is selection from the group consisting of halo and $C_1$–$C_4$ alkyl, and $R^2$ is selected from the group consisting of halo, $C_1$–$C_4$ alkyl, and $C_1$–$C_4$ alkoxycarbonyl.

It will be understood that the above preferred and especially preferred classes may be combined to form additional preferred and especially preferred classes.

The compounds of Formula II are antineoplastic agents. Thus, the present invention also provides a method of treating a susceptible neoplasm in a mammal that comprises administering to a mammal in need of said treatment an oncolytically effective amount of a compound of Formula II. The present compounds are believed to be useful in treating carcinomas such as neoplasms of the central nervous system: glioblastoma multiforme, astrocytoma, oligodendroglial tumors, ependymal and choroid plexus tumors, pineal tumors, neuronal tumors, medulloblastoma, schwannoma, meningioma, meningeal sarcoma; neoplasms of the eye: basal cell carcinoma, squamous cell carcinoma, melanoma, rhabdomyosarcoma, retinoblastoma; neoplasms of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors; neoplasms of the thorax: large cell lung carcinoma, small cell lung carcinoma, non-small cell lung carcinoma, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, veriform appendix and peritoneum, adneocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, addenocarcinoma of the uterine corpus, ovarian cancer, gynecologic sarcomas; neoplasms of the breast; neoplasms of the skin: basal cell carcinoma, squamous cell carcinoma, dermatofibrosarcoma, Merkel cell tumor; malignant melanoma; neoplasms of the bone and soft tissue:

osteogenic sarcoma, malignant fibrous histiocytoma, chondrosarcoma, Ewing's sarcoma, primitive neuroectodermal tumor, angiosarcoma; neoplasms of the hematopoietic system: myelodysplastic sydromes, acute myeloid leukemia, chronic myeloid leukemia, acute lymphocytic leukemia, HILV-1 and T-cell leukemia/lymphoma, chronic lymphocytic leukemia, hairy cell leukemia, Hodgkin's disease, non-Hodgkin's lymphomas, mast cell leukemia; and neoplasms of children: acute lymphoblastic leukemia, acute myelocytic leukemias, neuroblastoma, bone tumors, rhabdomyosarcoma, lymphomas, renal tumors. In particular, the present compounds are believed to be useful in treating solid tumors, especially tumors of the colon and rectum. It is preferred that the mammal to be treated by the administration of the compounds of Formula II is human.

The compounds of the present invention are acidic in nature and accordingly may react with any of a number of inorganic and organic bases, including amines and quaternary ammonium bases, to form pharmaceutically acceptable base addition salts. It is preferable to convert the compounds of Formula II to their pharmaceutically acceptable base addition salts for ease of administration when aqueous solutions of the subject compound are required. The Formula II compounds can react with basic materials such as alkali metal- or alkaline earth metal hydroxides, carbonates, and bicarbonates including, without limitation, sodium hydroxide, sodium carbonate, potassium hydroxide, calcium hydroxide, lithium hydroxide, etc. to form pharmaceutically acceptable salts such as the corresponding sodium, potassium, lithium, or calcium salt. The sodium and potassium salts are especially preferred.

Examples of amines suitable for forming salts are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, especially ethyl-, propyl-, diethyl- or triethylamine, but particulary isopropylamine and diethanolamine.

Examples of quaternary ammonium bases are in general the cations of haloammonium salts, for example the tetramethylammonium cation, the trimethylbenzylammonium cation, the triethylbenzylammonium cation, the tetraethylammonium cation or the trimethylethylammonium cation, but also the ammonium cation.

The compounds of the present invention may be prepared by methods well known to one of ordinary skill in the art. Generally, the N-[benzoyl]-phenylsulfonamides of Formula II are prepared by coupling an appropriately substituted phenylsulfonamide with an appropriately substituted benzoic acid or benzoic acid derivative as illustrated in the following scheme. The variables $R^1$, $R^2$, $R^{2a}$, $R^{2b}$, $R^3$, $R^{3a}$, and $R^4$ are as previously defined and Z is OH, Cl, Br, methanesulfonyloxy, or trifluoromethanesulfonyloxy.

Synthetic Scheme I

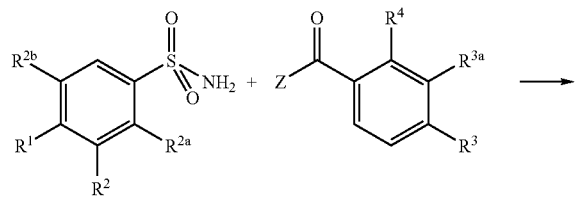

-continued

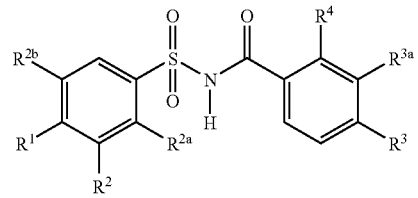

When Z is OH, the corresponding benzoic acid is coupled to the phenylsulfonamide under standard peptide coupling conditions well known to the skilled artisan. Specifically, the phenylsulfonamide and the benzoic acid are coupled in the presence of a peptide coupling reagent, optionally in the presence of a catalyst. Suitable peptide coupling reagents include N,N'-carbonyldiimidazole (CDI), N,N'-dicyclohexylcarbodiimide (DCC), 1-(3-dimethylaminopropyl)-3-ethylcarbodiimide hydrochloride (EDC), and 1-(3-(1-pyrrolidinyl)propyl)-3-ethylcarbodiimide (PEPC). Polymer supported forms of EDC (*Tetrahedron Letters*, 34(48), 7685 (1993)) and PEPC (U.S. Pat. No. 5,792,763) have been described, and are very useful for the preparation of the compounds of the present invention. Suitable catalysts for the coupling reaction include N,N-dimethyl-4-aminopyridine (DMAP). All of the reagents are combined in a suitable solvent, typically dichloromethane, chloroform, tetrahydrofuran, dioxane, or diethyl ether and are stirred for from 1 to 72 hours at a temperature of from ambient to about the reflux temperature of the solvent. The desired product may be isolated by standard extractive and crystallization techniques, and purified by chromatography or crystallization as necessary or desired. Where polymer-bound reagents are employed, they may be conveniently removed from the reaction mixture by filtration.

Alternatively, the sulfonamide may be reacted with a benzoic acid derivative, such as compounds where Z is chloro, bromo, methanesulfonyloxy, or trifluoromethanesulfonyloxy, in the presence of an acid scavenger such as pyridine, triethylamine, or a basic resin, optionally in the presence of a catalyst. The reagents are combined, and products isolated, essentially as described supra.

One skilled in the art would appreciate that compounds of Formula II where X is NH may be prepared as illustrated in Scheme II where $R^1$, $R^2$, $R^{2a}$, $R^{2b}$, $R^3$, $R^{3a}$, and $R^4$ are as previously defined.

Synthetic Scheme II

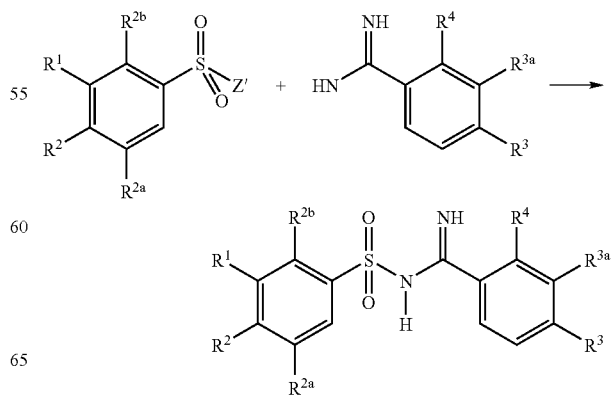

An appropriately substituted benzamidine is reacted with sulfonyl derivatives, such as compounds where Z' is chloro, bromo, methanesulfonyloxy, or trifluoromethanesulfonyloxy, in the presence of an acid scavenger such as pyridine, triethylamine, or a basic resin, optionally in the presence of a catalyst. The reagents are combined, and products isolated, essentially as described supra.

The requisite benzoic acids, benzoic acid derivatives, benzamidines, sulfonyl derivatives and sulfonamides are either commercially available or may be prepared by methods well known to the skilled artisan.

PREPARATION 1

2,4-dibromobenzonitrile

A solution of copper(I) cyanide (2.32 g, 25.9 mmol) in anhydrous dimethylsulfoxide (50 mL) is stirred at 60° C., and to this solution is added tert-butylnitrite (7.1 mL, 59.7 mmol) all at once. A solution of 2,4-dibromoaniline (5.0 g, 19.9 mmol) in anhydrous dimethylsulfoxide (30 mL) is added dropwise, via cannula, to the mixture. After the addition is complete the reaction mixture is stirred for 1 hr, cooled to 45° C., and then treated slowly with 5N HCl (50 mL). Five minutes later, the reaction mixture is cooled to ambient temperature and extracted with 1:1 ethyl acetate:hexane (2×300 mL). The combined organic layers are washed with water (100 mL) and saturated aqueous sodium chloride (100 mL), dried, concentrated under reduced pressure and the residue subjected to silica gel chromatography, eluting with hexane containing from 0–5% ethyl acetate. Fractions containing product are combined and concentrated under reduced pressure to provide the title compound (1.61 g, 31% yield).
mp=76–78° C.
FDMS: m/e=261 ($M^+$).

PREPARATION 2

2,4-dibromobenzoic acid

A stirred suspension of 2,4-dibromobenzonitrile (1.57 g, 6.0 mmol) in sulfuric acid (6 M, 150 mL) is heated to reflux for 3 days. The reaction mixture is cooled down to ambient temperature and then extracted with ethyl acetate (2×75 mL). The combined organic layers are washed with water (100 mL) and saturated aqueous sodium chloride (50 mL), dried, concentrated, then subjected to silica gel chromatography, eluting with chloroform containing 0.5% methanol and 0.1% acetic acid. Fractions containing product are combined and concentrated under reduced pressure to provide the title compound (0.81 g, 48% yield).
mp=171–172° C.
ESIMS: m/e=279 ($M^+$–1).

PREPARATION 3

2-bromo-chlorobenzoic acid

A solution of sodium nitrite (2.21 g) in water (15 mL) is added dropwise to a stirred ice-cooled mixture of 2-amino-4-chlorobenzoic acid (5.00 g, 29.1 mmol) and 48% hydrobromic acid (150 mL) in water (150 mL). The reaction mixture is stirred for 2 hr at 0° C. and is then treated dropwise with a solution of copper(II) bromide (7.81 g) in water (20 mL). Upon the completion of addition, the reaction mixture is allowed to warm to ambient temperature and is stirred overnight. The reaction mixture is then extracted with 3:1 ethyl acetate:hexane (2×400 mL). The combined organic layers are washed with saturated aqueous sodium chloride (200 mL), dried, concentrated under reduced pressure, and the residue subjected to silica gel chromatography, eluting with chloroform containing 1% methanol and 0.5% acetic acid. Fractions containing product are combined and concentrated under reduced pressure to provide the title compound (4.04 g, 59% yield).
mp=154–155° C.
ESIMS: m/e=233, 235 ($M^+$–1).

PREPARATION 4

4-sulfamoylbenzoic acid methyl ester

4-Carboxyphenylsulfonamide (2.00 g, 9.9 mmol) is suspended in 3:1 chloroform:methanol (200 mL). (Trimethylsilyl)-diazomethane is added as a 2.0 M solution in Hexanes (7.4 mL, 14.8 mmol) at ambient temperature and stirred for 5 min. The solution is concentrated in vacuo, and the crude is chromatographed on silica gel, 0.5% MeOH/0.1% AcOH in $CH_2Cl_2$. The product is a white solid, 2.11 g, 98% yield.
mp 180° C.
ESIMS m/e 214 ($M^+$–1).

PREPARATION 5

3,4-dibromophenylsulfonamide 3,4-Dibromo-phenylsulfonyl chloride (20 mmol; Aldrich) is suspended in 40 mL of 30% aqueous NHOH, and the mixture is stirred. Acetone is added slowly, portionwise, to form a homogeneous reaction mixture (5–10 mL). This addition is exothermic, with vigorous bubbling. The reaction is stirred at room temperature and monitored by ESI-MS. The mixture is concentrated by rotary evaporation to remove the acetone, and a solid formed. The solid is collected by suction filtration, washed with water, and allowed to air dry. The material is used as obtained, without further purification. ESIMS: 312, 314, 316 ($M^+$–1); mp 169–171° C.; lit mp 175–176° C. Huntress, E. H.: Carten, F. H. *J. Am. Chem. Soc.* 1940, 62, 511–514.

The compounds of PREPARATION 6–15 are prepared essentially as described in the procedure of PREPARATION 5.

| PREP. # | Product | Mass Spectral Data (m/e) |
|---|---|---|
| 6 | 3-chloro-4-fluoro-phenylsulfonamide | ESIMS: 210 ($M^+$ – 1) |
| 7 | 4-iodo-phenylsulfonamide | ESIMS: 284 ($M^+$ – 1) |
| 8 | 3,4-dichlorophenylsulfonamide | ESIMS m/e 224($M^-$ – 1; $^{35}Cl$, $^{35}Cl$) and 226 ($M^-$ – 1; $^{35}Cl$, $^{37}Cl$) and 228 ($M^-$ – 1; $^{37}Cl$, $^{37}Cl$) |
| 9 | 4-isopropylphenylsulfonamide | ESIMS m/e 198($M^-$ – 1) |
| 10 | 4-ethylphenylsulfonamide | ESIMS m/e 184($M^-$ – 1) |
| 11 | 3-trifluoromethyl-phenylsulfonamide | ESIMS: 224 ($M^+$ – 1) |
| 12 | 3-fluoro-phenylsulfonamide | ESIMS: 174 ($M^+$ – 1) |
| 13 | toluene-3-sulfonamide | ESIMS: 170 ($M^+$ – 1) |
| 14 | 3-bromophenylsulfonamide | ESIMS: 237 ($M^+$ – 1) |
| 15 | 4-bromophenylsulfonamide | ESIMS: 237 ($M^+$ – 1) |

PREPARATION 16

2-chloro-4-methylbenzoic acid

To 4-bromo-3-chlorotoluene (4.97 g, 24.2 mmol) in DMF (25 mL) is added Pd(OAc)$_2$ (0.54 g, 2.42 mmol), 1,3-bis(diphenylphosphino)propane (0.998 g, 2.42 mmol), triethylamine (12.5 mL) and methanol (12.5 mL). The reaction vessel is evacuated and purged three times with carbon monoxide gas. A balloon filled with carbon monoxide gas is used to maintain the carbon monoxide atmosphere. The reaction mixture is heated at 80° C. for 8 hr. After cooling H$_2$O (50 mL) is added. The mixture is extracted with hexanes (2×50 mL). The combined organic layers are dried over Na$_2$SO$_4$, filtered, concentrated and chromatographed with 0–3% EtOAc in hexanes. 1.24 g (28%) of methyl 2-chloro-4-methylbenzoate is isolated as a colorless oil. EIMS m/e 184 (M$^+$; $^{35}$Cl) and 186 (M$^+$; $^{37}$Cl).

To methyl 2-chloro-4-methylbenzoate (1.00 g, 5.42 mmol) in THF (10 mL) MeOH (5 mL) and H$_2$O (2.5 mL) is added 2N LiOH (8.12 mL, 16.2 mmol). The reaction mixture is heated at 50° C. for 2.5 hr, cooled to room temperature, then quenched with 5N HCl (3.24 mL). The mixture is concentrated to remove the TBF and MeOH. A white precipitate is formed and is filtered. After drying, 0.922 g (100%) of 2-chloro-4-methylbenzoic acid is isolated. ESIMS m/e 169 (M$^-$–1; $^{35}$Cl) and 171 (M$^-$–1; $^{37}$Cl).

PREPARATION 17

4-(tert-butyldimethylsilyloxy)phenylsulfonamide

4-Hydroxyphenylsulfonamide (3.46 g, 20 mmol) is dissolved in DMF (40 mL) and treated with tert-butyl-dimethylsilylchloride (3.31 g, 22.0 mmol) and imidazole (1.50 g, 22.0 mmol) at room temperature. After 20 hr, the reaction mixture is diluted with EtOAc (100 mL) and washed with 1.0 N HCl (2×50 mL). The organic phase is dried (MgSO4), filtered, and concentrated to yield an oil. The crude oil is purified by Biotage column chromatography (40M SiO$_2$ column, eluted at 75 mL/min with 1:1 hexanes:EtOAc). A white solid is obtained (4.24 g, 15.4 mmol, 77%). ESI-MS m/e 288.1 (M$^+$+H); mp 117–118° C.; $^1$H NMR (CDCl$_3$) δ 7.78 (d, 2H), 6.89 (d, 2H), 4.86 (br s, 2H), 0.97 (s, 9H), 0.20 (s, 6H).

PREPARATION 18

N-(2,4-dichlorobenzoyl)-4-(tert-butyldimethylsilyloxy)-phenylsulfonamide

To a stirring solution of 2,4-dichlorobenzoic acid (1.25 eq) in dry dichloromethane (10 mL/mmol), 4-(tert-butyldimethylsiloxy)phenylsulfonamide (1.0 eq) is added in one portion followed by EDC (1.25–1.5 eq) and finally, NN-dimethyl-4-aminopyridine (1.2 equiv). The mixture is vigorously stirred under nitrogen for 16 hr, concentrated under reduced pressure, and the residue partitioned between ethyl acetate and water. The organic layer is washed with 1N hydrochloric acid (4 times, 20 mL/mmol), then the combined aqueous phases extracted with ethyl acetate (twice, 20 mL/mmol). The combined organic layers are finally washed with water and saturated aqueous sodium chloride, dried over sodium sulfate and concentrated under reduced pressure. The residue is purified by silica gel chromatography or crystallization if necessary or desired. ESI-MS m/e 458.0 (M$^+$–H; 460.0 (M$^+$+H).

The compounds of PREPARATION 19–21 are prepared essentially as described in the procedure of PREPARATION 18.

| PREP. # | Product | Mass Spectral Data (m/e) |
|---|---|---|
| 19 | 3-Bromo-N-(2,4-dichlorobenzoyl)-phenylsulfonamide | ESI-MS m/e 409.0(M$^+$ – H) |
| 20 | 4-Iodo-N-(2,4-dichlorobenzoyl)-phenylsulfonamide | ESI-MS m/e 455.08(M$^+$ – H) |
| 21 | 4-Bromo-N-(2,4-dichlorobenzoyl)-phenylsulfonamide | ESI-MS m/e 409.0(M$^+$ – H) |

General Coupling Procedure

To a stirring solution of the benzoic acid (1.25 eq) in dry dichloromethane (10 mL/mmol), the phenylsulfonamide (1.0 eq) is added in one portion followed by EDC (1.25–1.5 eq) and finally, N,N-[dimethyl]4-aminopyridine (1.2 equiv). The mixture is vigorously stirred under nitrogen for 16 hr, concentrated under reduced pressure, and the residue partitioned between ethyl acetate and water. The organic layer is washed with 1N hydrochloric acid (4 times, 20 mL/mmol), then the combined aqueous phases extracted with ethyl acetate (twice, 20 mL/mmol). The combined organic layers are finally washed with water and saturated aqueous sodium chloride, dried over sodium sulfate and concentrated under reduced pressure. The residue may be subjected to silica gel chromatography or crystallization if necessary or desired.

The compounds of EXAMPLES 1–84 are prepared essentially as described in this general procedure.

| EXAMPLE # | Product | Mass Spectral Data (m/e) |
|---|---|---|
| 1 | N-[2,4-dichlorobenzoyl]-3-bromophenylsulfonamide | MS(ES): 408 [M – H]$^-$ |
| 2 | N-[2,4-dichlorobenzoyl]-3-chlorophenylsulfonamide | MS(ES): 362 [M – H]$^-$ |
| 3 | N-[2,4-dichlorobenzoyl]-4-methoxyphenylsulfonamide | MS(ES): 360 [M – H]$^-$ |
| 4 | N-[2,4-dibromobenzoyl]-4-methylphenylsulfonamide | ESIMS: 434 (M$^+$ $^{+\,1)}$ |
| 5 | N-[2,4-dibromobenzoyl]-4-tert-butylphenylsulfonamide | ESIMS: 476 (M$^+$ $^{+\,1)}$ |
| 6 | N-[2,4-dibromobenzoyl]-4-chlorophenylsulfonamide | ESIMS: 454, 456(M$^+$ + 1) |
| 7 | N-[2-bromo-4-chlorobenzoyl]-4-methylphenylsulfonamide | ESIMS: 388, 390(M$^+$ + 1) |
| 8 | N-[2-bromo-4-chlorobenzoyl]-4-chlorophenylsulfonamide | ESIMS: 408, 410(M$^+$ + 1) |
| 9 | N-[2,4-dichlorobenzoyl]-3-chloro-4-fluorophenylsulfonamide | ESIMS: 380(M$^+$ – 2), 382(M$^+$), 384(M$^+$ + 2) |
| 10 | N-[2-chloro-4-nitrobenzoyl]-4-chlorophenylsulfonamide | ESIMS: 373(M$^+$ – 2), 375(M$^+$), 377(M$^+$ + 2) |

-continued

| EXAMPLE # | Product | Mass Spectral Data (m/e) |
|---|---|---|
| 11 | N-[2-chloro-4-bromobenzoyl]-phenylsulfonamide | ESIMS: 372($M^+ - 2$), 374($M^+$) |
| 12 | N-[2-methyl-4-bromobenzoyl]-phenylsulfonamide | ESIMS: 352($M^+ - 2$), 354($M^+$) |
| 13 | N-[2-chloro-4-nitrobenzoyl]-phenylsulfonamide | ESIMS: 339($M^+ - 1$), 341($M^+ + 1$) |
| 14 | N-[2-chloro-4-bromobenzoyl]-4-bromophenylsulfonamide | ESIMS: 450($M^+ - 3$), 452($M^+ - 1$), 454($M^+ + 1$) |
| 15 | N-[2-chloro-4-nitrobenzoyl]-4-bromophenylsulfonamide | ESIMS: 417($M^+ - 2$), 419($M^+$) |
| 16 | N-[2-chloro-4-bromobenzoyl]-4-fluorophenylsulfonamide | ESIMS: 390($M^+ - 2$), 392($M^+$) |
| 17 | N-[2-chloro-4-bromobenzoyl]-3-chlorophenylsulfonamide | ESIMS: 406($M^+ - 3$), 408($M^+ - 1$), 410($M^+ + 1$) |
| 18 | N-[2-chloro-4-bromobenzoyl]-4-methoxyphenylsulfonamide | ESIMS: 402($M^+ - 2$), 404($M^+$), 406($M^+ + 2$) |
| 19 | N-[2-methyl-4-bromobenzoyl]-4-methoxyphenylsulfonamide | ESIMS: 382($M^+ - 2$), 384($M^+$) |
| 20 | N-[2-chloro-4-nitrobenzoyl]-4-methoxyphenylsulfonamide | ESIMS: 369($M^+ - 1$), 371($M^+$) |
| 21 | N-[2-chloro-4-nitrobenzoyl]-3,4-dichlorophenyl-sulfonamide | ESIMS: 407($M^+ - 2$), 409($M^+$), 411($M^+ + 2$) |
| 22 | N-[2-methyl-4-chlorobenzoyl]-3-chlorophenylsulfonamide | ESIMS: 342($M^- - 1$), 344($M^- - 1$), 346($M^- - 1$) |
| 23 | N-[2-methyl-4-chlorobenzoyl]-4-methylphenylsulfonamide | ES Negative Ion MS [M − H]$^-$ ions observed: m/z 342($^{35}$Cl, $^{35}$Cl), m/z 344 ($^{35}$Cl, $^{37}$Cl) and m/z 346 ($^{37}$Cl, $^{37}$Cl). |
| 24 | N-[2,4-dichlorobenzoyl]-3,4-dibromophenylsulfonamide | ES Negative Ion MS [M − H]$^-$ ions observed: m/z 322 ($^{35}$Cl) and m/z 324 ($^{37}$Cl). |
| 25 | N-[2,4-dichlorobenzoyl]-3-trifluoromethyl-phenylsulfonamide | ESIMS: 395.9476/395.9469 |
| 26 | N-[2,4-dichlorobenzoyl]-3-fluorophenylsulfonamide | ESIMS: 345.9508/345.9515 |
| 27 | N-[2,4-dichlorobenzoyl]-3-methylphenylsulfonamide | ESIMS: 365.9734/365.9747 |
| 28 | N-[2-methyl-4-bromobenzoyl]-4-chlorophenylsulfonamide | ESIMS m/e 386.0, 387.9, and 389.9 ($M^+ - 1$; $^{79}$Br, $^{35}$Cl; $^{79}$Br, $^{37}$Cl; $^{81}$Br, $^{37}$Cl) |
| 29 | N-[2-methyl-4-bromobenzoyl]-4-methylphenylsulfonamide | ESIMS m/e 366.0 and 368.0 ($M^+ - 1$; $^{79}$Br; $^{81}$Br) |
| 30 | N-[2-bromo-4-chlorobenzoyl]-4-methoxycarbonyl-phenylsulfonamide | ESIMS m/e 430.0, 431.9 and 433.9 ($M^+ - 1$; $^{35}$Cl, $^{79}$Br; $^{37}$Cl, $^{79}$Br; $^{37}$Cl, $^{81}$Br) |
| 31 | N-[2,4-dibromobenzoyl]-4-methoxycarbonyl-phenylsulfonamide | ESIMS m/e 473.8, 475.9, and 477.9 ($M^+ - 1$; $^{79}$Br, $^{79}$Br; $^{79}$Br, $^{81}$Br; $^{81}$Br, $^{81}$Br) |
| 32 | N-[2-bromo-4-chlorobenzoyl]-3-methoxycarbonyl-4-methoxyphenylsulfonamide | ESIMS m/e 459.9, 461.9, 463.9 ($M^+ - 1$; $^{79}$Br, $^{35}$Cl; $^{81}$Br, $^{35}$Cl; $^{81}$Br, $^{37}$Cl) |
| 33 | N-[2-bromo-4-chlorobenzoyl]-4-tert-butylphenylsulfonamide | ESIMS m/e 428.2, 430.2, and 432.2; ($M^+ - 1$; $^{79}$Br, $^{35}$Cl; $^{81}$Br, $^{35}$Cl; $^{81}$Br, $^{37}$Cl) |
| 34 | N-[2,4-dibromobenzoyl]-3-methoxycarbonyl-4-methoxyphenylsulfonamide | ESIMS m/e 503.9, 506.0 and 508.0; ($M^+ - 1$; $^{79}$Br, $^{79}$Br, $^{81}$Br; $^{79}$Br, $^{81}$Br, $^{81}$Br) |
| 35 | N-[2-methyl-4-bromobenzoyl]-3-chloro-4-fluorophenylsulfonamide | ESIMS m/e 404.0, 406.0, 408.0 ($M^+ - 1$; $^{79}$Br, $^{35}$Cl; $^{81}$Br, $^{35}$Cl; $^{81}$Br, $^{37}$Cl) |
| 36 | N-[2-methyl-4-bromobenzoyl]-4-iodophenylsulfonamide | ESIMS m/e 478.0 and 480.0 ($M^+ - 1$; $^{79}$Br; $^{81}$Br) |
| 37 | N-[2-methyl-4-bromobenzoyl]-3-methylphenylsulfonamide | ESIMS m/e 366.1 and 368.1 ($M^+ - 1$; $^{79}$Br; $^{81}$Br) |
| 38 | N-[2,4-dibromobenzoyl]-4-iodophenylsulfonamide | ESIMS m/e 541.9, 543.9 and 545.9 ($M^+ - 1$; $^{79}$Br, $^{79}$Br; $^{79}$Br, $^{81}$Br; $^{81}$Br, $^{81}$Br) |
| 39 | N-[2,4-dichlorobenzoyl]-4-iodophenylsulfonamide | ESIMS m/e 454 ($M^- - 1$; $^{35}$Cl, $^{35}$Cl) and 456 ($M^- - 1$; $^{35}$Cl, $^{37}$Cl) and 458 ($M^- - 1$; $^{37}$Cl, $^{37}$Cl) |
| 40 | N-[2-chloro-4-bromobenzoyl]-4-iodophenylsulfonamide | ES Negative Ion MS [M − H]$^-$ ions observed: m/z 498 ($^{79}$Br, $^{35}$Cl), m/z 500 ($^{81}$Br, $^{35}$Cl) and m/z 502 ($^{81}$Br, $^{37}$Cl). |
| 41 | N-[2-methyl-4-chlorobenzoyl]-4-methoxyphenylsulfonamide | ES Negative Ion MS [M − H]$^-$ ions observed: m/z 338 ($^{35}$Cl) and m/z 340 ($^{37}$Cl). |
| 42 | N-[2-methyl-4-chlorobenzoyl]-4-fluorophenylsulfonamide | ES Negative Ion MS [M − H]$^-$ ions observed: m/z 326 ($^{35}$Cl) and m/z 328 ($^{37}$Cl). |
| 43 | N-[2-methyl-4-chlorobenzoyl]-4-bromophenylsulfonamide | ES Negative Ion MS [M − H]$^-$ ions observed: m/z 386 ($^{79}$Br, $^{35}$Cl), m/z 388 ($^{81}$Br, $^{35}$Cl) and m/z 390 ($^{81}$Br, $^{37}$Cl). |
| 44 | N-[2-methyl-4-chlorobenzoyl]-2-methoxy-4-methylphenylsulfonamide | ES Negative Ion MS [M − H]$^-$ ions observed: m/z 352 ($^{35}$Cl) and m/z 354 ($^{37}$Cl). |

-continued

| EXAMPLE # | Product | Mass Spectral Data (m/e) |
|---|---|---|
| 45 | N-[2-methyl-4-chlorobenzoyl]-3-chloro-4-methylphenylsulfonamide | ES Negative Ion MS [M − H]$^-$ ions observed: m/z 356($^{35}$Cl, $^{35}$Cl), m/z 358 ($^{35}$Cl, $^{37}$Cl) and m/z 360 ($^{37}$Cl, $^{37}$Cl). |
| 46 | N-[2,4-bis-trifluoromethylbenzoyl]-4-fluorophenylsulfonamide | ES Negative Ion MS [M − H]$^-$ ion observed: m/z 414. |
| 47 | N-[2,4-bis-trifluoromethylbenzoyl]-4-methoxyphenylsulfonamide | ES Negative Ion MS [M − H]$^-$ ion observed: m/z 426. |
| 48 | N-[2,4-bis-trifluoromethylbenzoyl]-4-methylphenylsulfonamide | ES Negative Ion MS [M − H]$^-$ ion observed: m/z 410. |
| 49 | N-[2,4-bis-trifluoromethylbenzoyl]-4-bromophenylsulfonamide | ES Negative Ion MS [M − H]$^-$ ions observed: m/z 474 ($^{79}$Br) and m/z 476 ($^{81}$Br). |
| 50 | N-[2,4-bis-trifluoromethylbenzoyl]-3-methylphenylsulfonamide | ES Negative Ion MS [M − H]$^-$ ion observed: m/z 410. |
| 51 | N-[2-methyl-4-chlorobenzoyl]-4-trifluoromethoxy-phenylsulfonamide | ES Negative Ion MS [M − H]$^-$ ions observed: m/z 392 ($^{35}$Cl) and m/z 394 ($^{37}$Cl). |
| 52 | N-[2,4-bis-trifluoromethylbenzoyl]-3,4-dichlorophenyl-sulfonamide | ES Negative Ion MS [M − H]$^-$ ions observed: m/z 464 ($^{35}$Cl, $^{35}$Cl), m/z 466 ($^{35}$Cl, $^{37}$Cl) and m/z 468 ($^{37}$Cl, $^{37}$Cl). |
| 53 | N-[2,4-bis-trifluoromethylbenzoyl]-3,4-difluorophenyl-sulfonamide | ES Negative Ion MS [M − H]$^-$ ion observed: m/z 432. |
| 54 | N-[2-methyl-4-chlorobenzoyl]-3-chloro-4-fluorophenylsulfonamide | ES Negative Ion MS [M − H]$^-$ ions observed: m/z 360 ($^{35}$Cl, $^{35}$Cl), m/z 362 ($^{35}$Cl, $^{37}$Cl) and m/z 364 ($^{37}$Cl, $^{37}$Cl). |
| 55 | N-[2-methyl-4-chlorobenzoyl]-3-methylphenylsulfonamide | ES Negative Ion MS [M − H]$^-$ ions observed: m/z 322 ($^{35}$Cl) and m/z 324 ($^{37}$Cl). |
| 56 | N-[2-methyl-4-chlorobenzoyl]-4-iodophenylsulfonamide | ES Negative Ion MS [M − H]$^-$ ions observed: m/z 434 ($^{35}$Cl) and m/z 436 ($^{37}$Cl). |
| 57 | N-[2-methyl-4-chlorobenzoyl]-3,4-difluorophenyl-sulfonamide | ES Negative Ion MS [M − H]$^-$ ions observed: m/z 344 ($^{35}$Cl) and m/z 346 ($^{37}$Cl). |
| 58 | N-[2,4-bis-trifluoromethylbenzoyl]-3-chloro-4-fluorophenyl-sulfonamide | ES Negative Ion MS [M − H]$^-$ ions observed: m/z 448 ($^{35}$Cl) and m/z 450 ($^{37}$Cl). |
| 59 | N-[2-chloro-4-methylbenzoyl]-3-chloro-4-fluorophenyl-sulfonamide | ES Positive Ion MS [M + H]$^+$ ions observed: m/z 362 ($^{35}$Cl) and m/z 364 ($^{37}$Cl). |
| 60 | N-[2-methyl-4-chlorobenzoyl]-phenylsulfonamide | ES Positive Ion MS [M + H]$^+$ ions observed: m/z 310 ($^{35}$Cl) and m/z 312 ($^{37}$Cl). |
| 61 | N-[2-methyl-4-bromobenzoyl]-4-ethylthiophenyl-sulfonamide | ES Negative Ion MS [M − H]$^-$ ions observed: m/z 412 ($^{79}$Br) and m/z 414 ($^{81}$Br). |
| 62 | N-[2,4-dichlorobenzoyl]-4-ethylthiophenyl-sulfonamide | ES Negative Ion MS [M − H]$^-$ ions observed: m/z 388 ($^{35}$Cl, $^{35}$Cl), m/z 390 ($^{35}$Cl, $^{37}$Cl) and m/z 392 ($^{37}$Cl, $^{37}$Cl). |
| 63 | N-[2,4-bis-trifluoromethylbenzoyl]-4-isopropylphenyl-sulfonamide | ES Negative Ion MS [M − H]$^-$ ion observed: m/z 438. |
| 64 | N-[2-chloro-4-bromobenzoyl]-4-isopropylphenyl-sulfonamide | ES Negative Ion MS [M − H]$^-$ ions observed: m/z 414 ($^{79}$Br, $^{35}$Cl), m/z 416 ($^{81}$Br, $^{35}$Cl) and m/z 418 ($^{81}$Br, $^{37}$Cl). |
| 65 | N-[2,4-dibromobenzoyl]-4-ethylphenylsulfonamide | ES Negative Ion MS [M − H]$^-$ ions observed: m/z 444 ($^{79}$Br, $^{79}$Br), m/z 446 ($^{79}$Br, $^{81}$Br) and m/z 448 ($^{81}$Br, $^{81}$Br). |
| 66 | N-[2-methyl-4-bromobenzoyl]-4-ethylphenylsulfonamide | ES Negative Ion MS [M − H]$^-$ ions observed: m/z 380 ($^{79}$Br) and m/z 382 ($^{81}$Br). |
| 67 | N-[2,4-dibromobenzoyl]-4-isopropylphenyl-sulfonamide | ES Positive Ion MS [M + H]$^+$ ions observed: m/z 460 ($^{79}$Br, $^{79}$Br), m/z 462 ($^{79}$Br, $^{81}$Br) and m/z 464 ($^{81}$Br, $^{81}$Br). |
| 68 | N-[2,4-dichlorobenzoyl]-4-isopropylphenyl-sulfonamide | ES Negative Ion MS [M − H]$^-$ ions observed: m/z 370 ($^{35}$Cl, $^{35}$Cl), m/z 372 ($^{35}$Cl, $^{37}$Cl) and m/z 374 ($^{37}$Cl, $^{37}$Cl). |
| 69 | N-[2,4-dichlorobenzoyl]-4-ethylphenylsulfonamide | ES Negative Ion MS [M − H]$^-$ ions observed: m/z 356 ($^{35}$Cl, $^{35}$Cl), m/z 358 ($^{35}$Cl, $^{37}$Cl) and m/z 360 ($^{37}$Cl, $^{37}$Cl). |
| 70 | N-[2-methyl-4-chlorobenzoyl]-4-ethylphenylsulfonamide | ES Negative Ion MS [M − H]$^-$ ions observed: m/z 336 ($^{35}$Cl) and m/z 338 ($^{37}$Cl). |
| 71 | N-[2-chloro-4-bromobenzoyl]-4-ethylphenylsulfonamide | ES Negative Ion MS [M − H]$^-$ ions observed: m/z 400 ($^{79}$Br, $^{35}$Cl), m/z 402 ($^{81}$Br, $^{35}$Cl) and m/z 404 ($^{81}$Br, $^{37}$Cl). |

-continued

| EXAMPLE # | Product | Mass Spectral Data (m/e) |
|---|---|---|
| 72 | N-[2-bromo-4-chlorobenzoyl]-4-ethylphenylsulfonamide | ES Negative Ion MS [M − H]$^-$ ions observed: m/z 400 ($^{79}$Br, $^{35}$Cl), m/z 402 ($^{81}$Br, $^{35}$Cl) and m/z 404 ($^{81}$Br, $^{37}$Cl). |
| 73 | N-[2-bromo-4-chlorobenzoyl]-4-isopropylphenyl-sulfonamide | ES Negative Ion MS [M − H]$^-$ ions observed: m/z 414 ($^{79}$Br, $^{35}$Cl), m/z 416 ($^{81}$Br, $^{35}$Cl) and m/z 418 ($^{81}$Br, $^{37}$Cl). |
| 74 | N-[2-chloro-4-iodobenzoyl]-4-azidophenylsulfonamide | ESIMS m/e 460.9. (M − 1) |
| 75 | N-[2-methyl-4-chlorobenzoyl]-4-methylthiophenyl-sulfonamide | ES Positive Ion MS [M + H]$^+$ ions observed: m/z 356 ($^{35}$Cl) and m/z 358 ($^{37}$Cl). |
| 76 | N-[2-methyl-4-chlorobenzoyl]-4-trifluoromethylthio-phenylsulfonamide | ES Negative Ion MS [M − H]$^-$ ions observed: m/z 408 ($^{79}$Br, $^{35}$Cl), m/z 410 ($^{81}$Br, $^{35}$Cl) and m/z 412 ($^{81}$Br, $^{37}$Cl). |
| 77 | N-[2-methyl-4-chlorobenzoyl]-3-trifluoromethyl-phenylsulfonamide | ES Positive Ion MS [M + H]$^+$ ions observed: m/z 378 ($^{35}$Cl) and m/z 380 ($^{37}$Cl). |
| 78 | N-[2-methyl-4-bromobenzoyl]-3-trifluoromethyl-phenylsulfonamide | ES Positive Ion MS [M + H]$^+$ ions observed: m/z 422 ($^{79}$Br) and m/z 424 ($^{81}$Br). |
| 79 | N-[2-trifluoromethyl-4-methylbenzoyl]-4-methylphenyl-sulfonamide | ES Positive Ion MS [M + H]$^+$ ion observed: m/z 358. |
| 80 | N-[2,4-dichlorobenzoyl]-3-methoxyphenyl-sulfonamide | $^1$H NMR (CDCl3) δ 7.68–7.15 (m, 7 H); 3.80 (s, 3 H). |
| 81 | N-[2,4-dichlorobenzoyl]-4-trifluoromethyl-phenylsulfonamide | ESI-MS m/e 395.9 (M$^+$ − H) |
| 82 | N-[2,4-dichlorobenzoyl]-4-hydroxyphenyl-sulfonamide | Mp 155–157° C.; ESI-MS m/e 344.0 (M$^+$ − H) |
| 83 | N-[4-Bromo-2-methyl-benzoyl]-3,4-dimethyl-phenylsulfonamide | MS (ES): [M − H]$^-$ 379.9943 |
| 84 | N-[2,4-Bis-trifluoromethyl-benzoyl]-3-fluoro-phenylsulfonamide | MS (ES): [M − H]$^-$ 414.0049 |

EXAMPLE 85

N-[2-chloro-4-bromobenzoyl]-4-chlorophenylsulfonamide

An 8 mL reaction vial is charged with 2-chloro-4-bromobenzoic acid (0.39 mmol, 1.5 eq) and 2.0 mL of dichloromethane. A stock solution (4.0 mL) containing 4-chlorophenylsulfonamide (0.26 mmol, 1 eq) and N,N-[dimethyl]-4-aminopyridine (48 mg, 0.39 mmol, 1.5 eq) in dichloromethane is added, followed by 0.261 g carbodiimide polystyrene resin (2.0 mmol/g, 0.52 mmol, 2.0 eq, Novabiochem) and the vial is capped and rotated. After 72 hr, 0.77 g sulphonated polystyrene resin (NP-TsOH) is added (1.53 mmol/g, 1.17 mmol, Argonaut). After about 18 hr the reaction mixture is filtered and concentrated under a stream of nitrogen. The residue is subjected to reverse phase HPLC; CombiPrep column, YMC ODS-A 20×50 mm column with 5 micron, C18, 120 Angstrom pore size, gradient: 5% to 95% CH$_3$CN/0.01 HCl aqueous solution. Fractions containing product are combined and concentrated under reduced pressure to provide the title compound.

ESIMS: m/e=408(M$^+$+1), 406(M$^+$−1), 410(1$^+$+3).

The compounds of Examples 86–107 are prepared essentially as described in Example 85.

| EXAMPLE # | Product | Mass Spectral Data (m/e) |
|---|---|---|
| 86 | N-[2,4-dichlorobenzoyl]-4-methylphenylsulfonamide | ESIMS: 342(M$^+$ − 1), 344(M$^+$ + 1) |
| 87 | N-[2,4-dichlorobenzoyl]-4-methylthiophenylsulfonamide | ESIMS: 374(M$^+$ − 1), 376(M$^+$ + 1) |
| 88 | N-[2,4-dichlorobenzoyl]-4-tert-butylphenylsulfonamide | ESIMS: 384(M$^+$ − 1), 386(M$^+$ + 1) |
| 89 | N-[2,4-dichlorobenzoyl]-3-chloro-4-methylphenylsulfonamide | ESIMS: 378(M$^+$ + 1), 376(M$^+$ − 1), 380(M$^+$ + 3) |
| 90 | N-[2-methyl-4-chlorobenzoyl]-3-bromophenylsulfonamide | ESIMS: 388(M$^+$ + 1), 386(M$^+$ − 1), 390(M$^+$ + 3) |
| 91 | N-[2,4-dichlorobenzoyl]-4-fluorophenylsulfonamide | ESIMS: 346(M$^+$ − 1), 348(M$^+$ + 1) |
| 92 | N-[2,4-dichlorobenzoyl]-3,4-dichlorophenylsulfonamide | ESIMS: 398(M$^+$ + 1), 396(M$^+$ − 1), 400(M$^+$ + 3) |
| 93 | N-[2-methyl-4-chlorobenzoyl]-4-chlorophenylsulfonamide | ESIMS: 342(M$^+$ − 1), 344(M$^+$ + 1) |
| 94 | N-[2,4-dichlorobenzoyl]-4-bromo phenylsulfonamide | ESIMS: 408(M + 1), 406(M − 1), 410(M + 3) |
| 95 | N-[2,4-dichlorobenzoyl]-4-methylsulfonyloxyphenyl-sulfonamide | ESIMS: 422 (M − 2), 424 (M), 426 (M + 2) |
| 96 | N-[2,4-dichlorobenzoyl]-4-trifluoromethoxyphenyl-sulfonamide | ESIMS: 412 (M − 2), 414 (M), 416 (M + 2) |
| 97 | N-[2,4-dichlorobenzoyl]-4-methoxy-3,5-dimethylphenylsulfonamide | ESIMS: 368 (M − 2), 370 (M), 372 (M + 2) |
| 98 | N-[2,4-dichlorobenzoyl]-4-dimethylaminophenyl-sulfonamide | ESIMS: 371 (M − 2), 373 (M) |
| 99 | N-[2,4-bis-trifluoromethylbenzoyl]-4-chlorophenylsulfonamide | ESIMS: 430 (M − 1), 432 (M + 1) |
| 100 | N-[2-methyl-4-bromobenzoyl]-4-bromophenylsulfonamide | ESIMS: 430 (M − 3), 432 (M − 1), 434 (M + 1) |
| 101 | N-[2-chloro-4-nitrobenzoyl]-4-fluoro-phenylsulfonamide | ESIMS: 357 (M − 1) |

-continued

| EXAMPLE # | Product | Mass Spectral Data (m/e) |
|---|---|---|
| 102 | N-[2-chloro-3-methylbenzoyl]-4-chlorophenylsulfonamide | ESIMS: 342 (M − 1) 344 (M + 1) |
| 103 | N-[2,4-dichlorobenzoyl]-4-nitrophenylsulfonamide | ESIMS: 373 (M − 1) 375 (M + 1) |
| 104 | N-[2-methyl-4-chlorobenzoyl]-3,4-dichlorophenylsulfonamide | ESIMS: 378 (M + 1) 376 (M − 1) 380 (M + 3) |
| 105 | N-[2-methyl-4-chlorobenzoyl]-4-tert-butylphenylsulfonamide | ESIMS: 364 (M − 1) 366 (M + 1) |
| 106 | N-[2-methyl-4-chlorobenzoyl]-3-cyanophenylsulfonamide | ESIMS: 333 (M − 1) |
| 107 | N-[2,4-dichlorobenzoyl]-4-[1,2,4]triazol-4-yl-phenylsulfonamide | 395 (M) |

EXAMPLE 108

N-[2,4-dichlorobenzoyl]-4-(1-methylsulfanylo-phen-4-yl)phenylsulfonamide

Step A: Procedure for Activation of the Resin

The Rink amide resin (CA Novabiochem, 0.53 mmol/g) was suspended in a 30% solution of pyridine in DMF and stirred at room temperature for 3 hours. The mixture was filtered and the resin was washed twice with DMF and then, alternatively with $CH_2Cl_2$ and MeOH. The activated resin having a free amino group was dried and used without further purification.

The Rink amide resin (0.53 mmol/g) was suspended in a 1:1 mixture $CH_2Cl_2$/THF and $Et_3N$ (4 eq), 4-iodophenyl-sulfonamide (3 eq) and DMAP (catalytic amount). The solution was stirred overnight at room temperature. The mixture was filtered and the resin was washed alternatively with $CH_2Cl_2$ and MeOH. The 4-iodophenylsulfonamide Rink resin was dried under vacuum.

The corresponding 4-iodophenylsulfonarmide Rink resin (0.26 mmol, 0.53 mmol/g), Methylsulfanyl-phenyl boronic acid (2 eq), potassium carbonate (6 eq) and the Palladium acetate (0.5 eq) were mixed together and suspended in 7 mL of a mixture dioxane/water 6:1. This mixture was heated in an Argovant® QUEST® 210 at 100° C. for 24 hours. Then, the resin was washed twice with 5 mL of a mixture dioxane/water 6:1 and then six times with $CH_2Cl_2$ (7 nL) followed each time by MeOH (7 mL).

3 mL of a 95% aqueous solution of trifluoroacetic acid were added to the resin previously dissolved in 3 mL of $CH_2Cl_2$. The mixture was stirred for 30 min at room temperature, filtered as described above. The 4'-methylsulfanyl-biphenylsulfonamide was employed without further purification.

To a stirred solution of 2,4-Dichloro-benzoic acid (1.25 eq) in dry $CH_2Cl_2$ (10 ml/mmol), 4'-Methylsulfanyl-biphenyl-4-sulfdnamide (1.0 eq) was added in one portion followed by EDC (1.25 or 1.5 eq) and finally, DMAP (1.2 equiv). The mixture was vigorously stirred under nitrogen for 16 hours, then evaporated in vacuo and the residue partitioned between EtOAc and water. The organic layer was washed with 1N HCl (4 times, 20 mL/mmol), then the aqueous phase was extracted with EtOAc (twice, 20 mL/mmol). The combined organic layers were finally washed with water and brine, dried over $Na_2SO_4$ and concentrated in vacuo. The crude product was purify by silica gel chromatography using the appropriate eluent afford the title compound.

ESI-MS ($M^+$–H) 450.9870/450.0.

EXAMPLE 109

N-[2,4-dichlorobenzoyl]-4-3'-acetyl-biphenylsulfonamide

A suspension of 4-iodophenylsulfonamide Rink resin (0.26 mmol, 0.53 mmol/g), 3-acetylphenyl boronic acid (2 eq) and 2,4-dichloro-benzoic acid (1.25 eq); were used essentially as described in Example 108 to prepare the title compound.

ESI-MS ($M^+$–H) 447.0099/446.0.

EXAMPLE 110

N-[2,4-dichlorobenzoyl]phenylsulfonamide

To a mixture of phenylsulfonamide (0.16 mol; 25.12 g) and potassium carbonate (0.2 mol; 27.6 g) in 500 mL dioxane is added dropwise 2,4-dichlorobenzoyl chloride (0.13 mole; 18.0 mL). The mixture is warmed to reflux under nitrogen for 16 hr. The reaction is then diluted with water (500 mL), neutralized to pH 5 with concentrated hydrochloric acid, and extracted 3 times with ethyl acetate. The combined ethyl acetate layers are washed with saturated aqueous sodium chloride, dried over sodium sulfate and concentrated under reduced pressure to a white solid. The solid residue is subjected to silica gel chromatography, eluting with dichloromethane containing from 0–5% methanol. Fractions containing the product are combined and concentrated under reduced pressure to provide the title compound.

MS(ES): m/e=329.9 ($M^+$+1), 327.9 ($M^+$−1).

EXAMPLE 111

N-[2,4-dichlorobenzoyl]-4-chlorophenylsulfonamide

A mixture of 4-chlorophenylsulfonamide (0.1 mol; 19.0 g) and 2,4-dichlorobenzoyl chloride (0.12 mol; 16.8 mL); the title compound was prepared essentially as described in Example 110.

MS(ES): m/e=363.9 (M+)

EA: Calculated for $C_{13}H_8Cl_3NO_3S$: Theory: C, 42.82; H, 2.21; N, 3.84. Found: C, 42.56; H, 2.14; N, 3.76.

EXAMPLE 112

25 N-[2-chloro-4-bromobenzoyl]-4-chlorophenylsulfonamide

To a reaction mixture of 4-chlorophenylsulfonamide (15.6 g, 81.4 mmol), CDI (15.82 g, 97.7 mmol) and ethyl acetate (300 mL) at room temperature is added a slurry of 2-chloro-4-bromobenzoic acid (23.0 g, 97.7 mmol) in ethyl acetate (100.0 mL) over a period of 15.0 min (note: gas evolution is observed which can be controlled by the rate of addition of the slurry; reaction mixture goes into solution by the end of addition of the slurry; reaction can be monitored by HPLC or TLC with 1:1 ethyl acetate/heptane eluent. The reaction is then stirred at room temperature for 30 min and then heated at 60° C. for 90 min or until no gas evolution is observed. The reaction is cooled to 40° C., and 1,8-diazabicyclo[5.4.0]undec-7-ene is (14.63 mL) added (all at once). The reaction temperature goes from 40° C. to 45° C. The mixture is stirred until it reaches room temperature before quenching with deionized water (400 mL). The top organic layer is separated, washed with 1N HCl (300.0 mL), dried with anhydrous $MgSO_4$, filtered and the cake washed with ethyl acetate (20.0 mL). The filtrate is concentrated to 50.0 g of syrupy solution, then heptane (250.0 mL) is added with vigorous stirring. With heating, a white slurry is formed and is refluxed and then allowed to equilibrate to room temperature. The white precipitate is filtered and the cake is washed with heptane (20.0 mL). The precipitate is dried in a house vacuum at 55° C. for 18 hr. (mass=29.12 g, 87.4% wt yield).

A mixture of 19.17 g of the product and 1:2 ethyl acetate/heptane (150.0 mL) is heated at reflux for 30 min, and then cooled to room temperature. The off white precipitate is filtered and then the cake is washed with heptane (50.0 mL). The precipitate is dried in a house vacuum at 50° C. for 18 hr. (mass=14.93 g; 78% recovery).

ESIMS: m/e=408($M^+$+1), 406($M^+$−1), 410($M^+$+3).

EXAMPLE 113

N-[2-chloro-4-bromobenzoyl]-4-chlorophenylsulfonamide sodium salt

To a solution of N-[2-chlorobromobenzoyl]-4-chlorophenylsulfonamide (5.2 g, 12.72 mmol) and tert-butyl methyl ether (88.0 mL) at room temperature is added sodium methoxide (0.69 g, 12.72 mmol) all at once. The reaction is then stirred for 5 hr, after which heptane (88.0 mL) is added followed by vigorous stirring for 60 min. A white precipitate is formed, filtered off under a positive nitrogen pressure, and the cake subsequently washed with heptane (2×44.0 mL). The cake is dried to semi-dryness, followed by drying in a house vacuum oven at 130° C. for 18 hr (mass=4.4 g, 80% wt. Yield; $^1$H nmr (DMSO $d_6$) 7.8–7.85 (m, 1H), 7.81–7.82 (m, 1H), 7.58–7.59 (d, 1H, J=1.76 Hz), 7.51–7.52 (m, 1H), 7.48–7.49 (m, 1H), 7.44–7.45 (d, 1H, J=1.76) 7.37–7.4 (d, 1H).

EXAMPLE 114

N-[3-chloro-4-fluorophenylsulfonyl]-3-fluoro-4-methylbenzamidine

Add 3-fluoro-4-methylbenzamidine hydrochloride (0.025 g, 0.133 mmol) in THF (0.5 mL) to 3-chloro-4-fluorophenyl sulfonylchloride (0.0304 g, 0.133 mmol) followed by N-methylmorpholine (0.2 mL). The reaction mixture was concentrated and chromatographed using reverse phase chromatography (gradient of 5–95% (0.1% TFA in CH3CN) in (0.1% TFA in $H_2O$). A white solid (16.4 mg, 36%) was isolated. ES Positive Ion MS [M+H]$^+$ ions observed: m/z 345 ($^{35}$Cl) and m/z 347 ($^{37}$Cl).

EXAMPLE 115

N-[3-chloro-4-fluorophenylsulfonyl]-4-chlorobenzamidine 4-chlorobenzamidine hydrochloride (0.025 g, 0.133 mmol) and 3-chloro-4 fluorophenyl sulfonylchloride (0.0304 g, 0.133 mmol); were used essentially as described in Example 114 to prepare the title compound. ES Positive Ion MS [M+H]$^+$ ions observed: m/z 347 ($^{35}$Cl, $^{35}$Cl), m/z 349 ($^{37}$Cl, $^{37}$Cl) and m/z 351 ($^{37}$Cl, $^{37}$Cl).

EXAMPLE 116

N-[3-chloro-4-fluorophenylsulfonyl]-3-chloro-4-fluorobenzamidine

A mixture of 3-chloro-4-fluorobenzamidine hydrochloride (0.025 g, 0.133 mmol) and 3-chloro-4-fluorophenyl sulfonylchloride (0.0304 g, 0.133 mmol); the title compound is prepared essentially as described in Example 115. ES Positive Ion MS [M+H]$^+$ ions observed: m/z 365 ($^{35}$Cl, $^{35}$Cl), m/z 367 ($^{35}$Cl, $^{37}$Cl) and m/z 369 ($^{37}$Cl, $^{37}$Cl).

EXAMPLE 117

N-[2,4-dichlorobenzoyl]-4-hydroxyphenylsulfonamide

4-Methoxy-phenyl-4-sulfonamide (0.0608 g, 0.132 mmol) is dissolved in THF (1.25 mL) and treated with tetrabutylammonium fluoride (1.0 N/THF; 200 μL, 2.0 mmol) at room temperature with stirring for 18 hr. The reaction mixture is diluted with EtOAc (10 mL) and washed with saturated aq. $NH_4Cl$ (1 mL), $H_2O$ (2×1 nm), and brine (1 mL). The organic phase is dried MgSO4, filtered, and concentrated by rotary evaporation. (Lyopholized from $H_2O$/MeOH to obtain a glassy solid, 20 mg (0.058 mmol, 58%). Purified by preparative HPLC.) mp 155–157° C.; ESI-MS m/e 344.0 (M+−H); $^1$H NMR (d6-DMSO) 7.90 (d, 2H); 7.68 (s, 1H); 7.44 (s, 2H); 6.90 (d, 2H); 3.43 (br s, 3H).

EXAMPLE 118

N-[2,4-dichlorobenzoyl]-4-(thien-3-yl)-phenylsulfonamide

To a solution of N-(2,4-dichlorobenzoyl)-4-iodo-phenylsulfonamide (0.10 mmol) in toluene/ethanol 20/1 (3 mL) is added 3-thiopheneboronic acid (0.18 mmol, 0.18 mL, 1.0M solution in DMF) and tetrakis-(triphenylphosphine) palladium (0) (10 mol %). Then 2M aqueous $Na_2CO_3$ is added (0.3 mL) and the stirred mixture is heated to 100° C. overnight (17 hr)(Buchi Syncore system). The reaction mixture is concentrated (Genevac apparatus), then water is added (2.5 mL) and ethyl acetate (5 mL). The phases are separated and the aqueous layer is extracted with ethyl acetate (3×5 mL). This process is automatically carried out using a Tecan system. The solvents are evaporated and the corresponding crude product is purified by HPLC to give the title compound.

ESI-MS m/e 410.96/410.0 [M+−H]

The compounds of EXAMPLES 119–130 are prepared essentially as described in the procedure for EXAMPLE 118.

| EXAMPLE # | Product | Mass Spectral Data (m/e) |
|---|---|---|
| 119 | N-[2,4-dichlorobenzoyl]-4-(1-trifluoromethylphen-4-yl)phenylsulfonamide | ESI-MS m/e 472.99/472.2 [$M^+$ − H] |

-continued

| EXAMPLE # | Product | Mass Spectral Data (m/e) |
|---|---|---|
| 120 | N-[2,4-dichlorobenzoyl]-4-(1-fluoro-phen-3-yl)-phenylsulfonamide | ESI-MS m/e 422.99/422.0 [M$^+$ − H] |
| 121 | N-[2,4-dichloro-benzoyl]-4-furan-2-yl-phenylsulfonamide | ESI-MS m/e 394.98/394.2 [M$^+$ − H] |
| 122 | N-[2,4-dichlorobenzoyl]-4-(1-methoxy-phen-2-yl) phenylsulfonamide | ESI-MS m/e 435.01/434.0 [M$^+$ − H] |
| 123 | N-[2,4-dichlorobenzoyl]-4-(1-methoxycarbonyl-phen-4-yl)phenylsulfonamide | ESI-MS m/e 447.07/446.0 [M$^+$ − H] |
| 124 | N-[2,4-dichlorobenzoyl]-4-quinolin-8-yl-phenylsulfonamide | ESI-MS m/e 456.01/455.1 [M$^+$ − H] |
| 125 | N-[2,4-dichloro-benzoyl]-3-quinolin-8-yl-phenylsulfonamide | ESI-MS m/e 456.01/457.2 [M$^+$ + H] |
| 126 | N-[2,4-dichlorobenzoyl]-4-fur-3-yl-phenylsulfonamide | ESI-MS m/e 394.98/394.0 [M$^+$ − H] |
| 127 | N-[2,4-dichloro-benzoyl]-4-pyridin-3-yl-phenylsulfonamide | ESI-MS m/e 406.0 [M$^-$ − H] |
| 128 | N-[2,4-dichloro-benzoyl]-3-biphenylsulfonamide | ESI-MS m/e 405.1 [M$^-$ − H] |
| 129 | N-[2,4-dichloro-benzoyl]-4'-methoxy-4-biphenylsulfonamide | ESI-MS m/e 435.2 [M$^-$ − H] |
| 130 | N-[2,4-dichlorobenzoyl]-4-thiophen-2-yl-phenylsulfonamide | ESI-MS m/e 411.1 [M$^-$ − H] |

All of the compounds concerned are orally available and are normally administered orally, and so oral administration is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula II may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent for capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate; disintegrating agents such as: croscarmellose, crospovidone, sodium starch glycolate, corn starch and the like; lubricants such as: magnesium stearate, steric acid, talc or hydrogenated vegetable oil; glidants such as colloidal silicon dioxide; wetting agents such as: sodium lauryl sulfate and polysorbate 80 (CAS No. 9005-65-6); and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

Injections for parenteral administration include sterile aqueous or non-aqueous solutions, suspensions and emulsions. Aqueous solutions and suspensions may include distilled water for injection or physiological salt solution. Non-aqueous solutions and suspensions may include propylene glycol, polyethylene glycol, vegetable oil such as olive oil, alcohol such as ethanol or polysorbate 80. Injections may comprise additional ingredients other than inert diluents: e.g. preserving agents, wetting agents, emulsifying agents, dispersing agents, stabilizing agents (such as lactose), assisting agents such as agents to assist dissolution (e.g. glutamic acid or aspartic acid). They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile diluent(s) for injection immediately before use.

The compounds of Formula II are generally effective over a wide dosage range. For example, dosages per day normally fall within the range of about 10 to about 300 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way.

It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

Inhibition of HUVEC Proliferation

Human umbilical vein endothelial cells (JC; BioWhittaker/Clonetics, Walkersville, Md.) were maintained in endothelial cell growth medium (EGM) containing basal medium (EBM) with bovine brain extract, human epidermal growth factor, hydrocortisone, gentamicin, amphotericin B and 2% fetal bovine serum. For the assay, HUVEC ($5\times10^3$) in EBM (200 µl) with 0.5% fetal bovine serum were added to wells in a 96-well cell culture plate and incubated at 37° C. for 24 hr in humidified 5% carbon dioxide/air. The test compounds were serially diluted in dimethyl sulfoxide (DMSO) in concentrations from 0.0013 to 40 µM and added to the wells in 20 µl. Then human vascular endothelial growth factor (VEGF) (20 ng/mL in wells; R&D Systems, Minneapolis, Minn.) prepared from a stock solution of 100 µg/mL in phosphate buffered normal saline containing 0.1% bovine serum albumin, was added to the wells. The HUVEC were incubated at 37° C. for 72 hr in humidified 5% carbon dioxide/air. WST-1 cell proliferation reagent (20 µL; Boehringer Mannheim, Indianapolis, Ind.) was added to the wells and the plates returned to the incubator for 1 hr. The absorbance of each well at 440 nm was measured. The growth fraction was determined from the absorbance of treated wells with and without VEGF divided by the absorbance obtained from control wells set to zero and 1.0. The exemplified compounds were tested in this assay and all exhibited an $IC_{50} \leq 1.0$ µM.

Rat Corneal Micropocket Assay

Fisher 344 female rats (145–155 grams; Taconic, Inc., Germantown, N.Y.) were anesthesized with acepromazine (2.5 mg/kg, ip) 20 minutes prior to initiation of 2–3% isoflurane/oxygen inhalation. The body temperature was maintained with a circulating hot water pad. The surgery was performed using an ophthalmic operating microscope (OMS.75 Operating Microscope, TopCon Corporation, Japan). A scalpel blade (#15) was used to make a vertical half-thickness linear corneal incision just lateral to the center of the eye. The tip of the scalpel blade was used to gently undermine the superior corneal layer of the cornea nearest to the limbus. A pocket was formed in the cornea using blunt dissection with corneal scissors (Roboz, Rockville, Md.). Nitrocellulose filters (0.45 µM, Millipore, Bedford, Mass.) were cut into small disks using a 20 gauge needle punch. The disks were soaked in 2 µl of human VEGF solution (0.82 µg/l; R&D Systems) or human basic fibroblast growth factor (0.20 µg/µl; R&D Systems) for 10 minutes on ice. Using forceps, the disks impregnated with the angiogenic factor (VEGF or bFGF) were inserted into the corneal pocket so that the disk is firmly covered with corneal epithelium. The animals were treated with the compound of Example 110 (160 mg/kg) administered orally by gavage in phosphate buffered saline once per day on days 1 through 10 post implantation of the disks. The eyes were photographed on days 7 and 14 post implantation of the disks. For photography, the animals were treated with atropine sulfate (AmTech Group, Inc., Phoenix Scientific, Inc., St. Joseph, Mo.) topically for mydriasis and anesthetized with 2–3% isoflurane/oxygen. The eyes were photographed using the ophthalmic microscope and the images were saved using Image Pro-Plus software. The images were analyzed by converting the area of interest to high contrast black and white reversed image and counting the bright pixels as a determination of the vascular area. The data are images from at least 6 eyes. The compound of Example 110 was a very effective inhibitor of VEGF-induced neoangiogenesis, but was not an effective inhibitor of bFGF-induced neoangiogenesis.

HCT116 Colon Carcinoma Cell Growth Inhibition

HCT116 colon carcinoma cells were grown monolayer culture in RPMI 1640 medium supplemented with 10% fetal bovine serum and 1% penicillin-streptomycin (GibcoBRL, Grand Island, N.Y.). HCT116 cells in exponential growth phase were exposed to various concentrations of the test compounds at 37° C. for 72 hr in 5% carbon dioxide/air. After exposure to the agent, the cells were washed with 0.9% phosphate buffered saline. Growth inhibition was determined using WST-1 cell proliferation reagent as described above. The results are expressed as the growth fraction of treated cells compared with control cultures. Representative compounds of the present invention were tested for efficacy against the human colon HCT116 tumor cells. The data from these experiments are summarized in TABLE I.

TABLE I

| EXAMPLE | $IC_{50}$ (µM) | EXAMPLE | $IC_{50}$ (µM) |
|---|---|---|---|
| 1 | 4.2 | 62 | 19.3 |
| 3 | 2.5 | 63 | 24.7 |
| 5 | 3.8 | 64 | 18.2 |
| 6 | 4.0 | 70 | 16.9 |
| 9 | 1.7 | 73 | 8.3 |
| 10 | 12.1 | 79 | 5.2 |
| 11 | 5.5 | 80 | 12.3 |
| 14 | 40.0 | 81 | 11.3 |
| 15 | 10.4 | 82 | 12.4 |
| 16 | 3.8 | 86 | 1.6 |
| 17 | 15.8 | 87 | 5.5 |
| 18 | 9.3 | 88 | 4.8 |
| 20 | 2.4 | 89 | 4.8 |
| 21 | 30.4 | 90 | 4.5 |
| 23 | 15.9 | 92 | 17.4 |
| 24 | 37.1 | 93 | 18.1 |
| 25 | 9.6 | 94 | 3.6 |
| 26 | 6.1 | 95 | 4.3 |
| 30 | 10.1 | 96 | 34.7 |
| 32 | 7.8 | 97 | 7.0 |
| 33 | 7.8 | 98 | 13.0 |
| 34 | 16.5 | 99 | 33.5 |
| 35 | 17.0 | 100 | 9.2 |
| 36 | 28.4 | 101 | 12.4 |
| 37 | 15.5 | 102 | 6.3 |
| 38 | 13.9 | 103 | 11.9 |
| 41 | 14.5 | 104 | 22.2 |
| 42 | 3.3 | 105 | 14.8 |
| 44 | 18.7 | 106 | 4.6 |
| 45 | 20.7 | 108 | 16.0 |
| 46 | 4.8 | 109 | 25.1 |
| 47 | 8.7 | 110 | 3.5 |
| 49 | 14.7 | 111 | 15.0 |
| 50 | 10.5 | 112 | 2.8 |
| 51 | 26.7 | 115 | 33.6 |
| 53 | 11.2 | 116 | 5.9 |
| 55 | 9.5 | 117 | 12.4 |
| 56 | 16.8 | 121 | 24.5 |
| 57 | 5.0 | 122 | 25.8 |
| 59 | 15.0 | 123 | 37.7 |
| 60 | 6.6 | 124 | 5.6 |
| 61 | 14.2 | 126 | 18.5 |

Conventional Murine Tumor and Human Tumor Xenouraft Assays

Inhibition of tumors transplanted into mice is an accepted procedure for studying the efficacy of antitumor agents (Corbett, et al., *In vivo Methods for Screening and Preclinical Testing; Use of rodent solid tumors for drug discovery.*, In: Anticancer Drug Development Guide: Preclinical Screening, Clinical Trials, and Approval, B. Teicher (ed), Humana Press Inc., Totowa, N.J., Chapter 5, pages 75–99 (1997); (Corbett, et al., *Int., J. Parmacog.*, 33, Supplement, 102–122 (1995)). Murine tumors or human xenographs were implanted essentially as described by Corbett in *In vivo Methods for Screening and Preclimical Testing; Use of rodent solid tumors for drug discovery*. Briefly, the murine tumor or human xenograph was implanted subcutaneously using either 12-gauge trocar implants or counted number of cells. The location for the trocar insertion is midway between the axillary and inguinal region along the side of the mouse. The trocar is slipped approximately ¾ of an inch subcutaneously up toward the axilla before discharging the tumor fragment, and pinching the skin as the trocar is removed., Alternatively, human tumor cells prepared from a brie of donor tumors ($5 \times 10^6$ cells) were implanted subcutaneously in a hind-leg of a male or female nude mouse (Charles River). Either a test compound in vehicle or vehicle alone was administered by intravenous bolus injection (iv), intraperitoneal injection (ip), or oral gavage (po). Each treatment group, as well as a group of untreated control animals, consisted of five animals per group in each experiment. Subcutaneous tumor response was monitored by tumor volume measurement performed twice each week over the course of the experiment (60–120 days). Body weights were taken as a general measure of toxicity. The subcutaneous tumor data were analyzed by determining the median tumor weight for each treatment group over the course of the experiment and calculating the tumor growth delay as the difference in days for the treatment versus the control tumors to reach a volume of either 500 or 1000 $mm^3$.

The compound of Example 110 was tested against a variety of murine and human tumors substantially as described supra. The data from these tests are summarized in TABLES II–XIII. The parameters measured in each experiment are summarized in the following paragraphs.

Tumor Weight(mg)=$(a \times b^2)/2$ where a=tumor length (mm) and b=tumor width (mm).

Tumor Growth Delay=T−C where T is the median time (days) required for the treatment group tumors to reach a predetermined size, and C is the median time (days) for the control group tumors to reach the same size. Tumor-free survivors are excluded from this calculation, and are tabulated separately (Tumor Free).

$$\text{Log Kill} = \frac{\text{Tumor Growth Delay}}{(3.32)(Td)}$$

where Tumor Growth Delay is as previously defined and Td is tumor volume doubling time (days), estimated from the best fit straight line from a log-linear growth plot of the control group of tumors in exponential growth (100–800 mg range)

% T/C mass—The treatment and control groups are measured when the control group tumors reach approximately 700 to 1200 mg in size (median group). The median tumor weight of each group is determined (including zeros). The T/C value in percent is an indication of antitumor effectiveness. A T/C≦42% is considered significant antitumor activity. A T/C<10% is considered to indicate highly significant antitumor activity.

Body Weight Loss Nadir—A body weight loss nadir (mean of group) of greater than 20% or drug deaths greater than 20% are considered to indicate an excessively toxic dosage in single course trials.

Activity Rating—the Activity Rating is derived from the Log Kill according to the following table:

| ANTITUMOR ACTIVITY | LOG KILL | ACTIVITY RATING |
|---|---|---|
| HIGHLY ACTIVE | >2.8 | ++++ |
|  | 2.0–2.8 | +++ |
|  | 1.3–1.9 | ++ |
|  | 0.7–1.2 | + |
| INACTIVE | <0.7 | − |

TABLE II

EARLY STAGE MURINE COLON ADENOCARCINOMA-38
(BDF1 male mice, CRL-Raleigh)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 144 | ACTIVITY RATING |
|---|---|---|---|---|---|---|---|
| 0 | +6.3% | 0/5 | — | — | — | 0/5 | − |
| 1200[a] | −5.2% | 0/6 | 0% | All cures | >4.5 | 6/6 | ++++ |
| 920[b] | +7.7% | 0/5 | 0% | All cures | >4.5 | 5/5 | ++++ |
| 272[c] | +3.1% | 0/5 | 0% | All cures | >4.5 | 5/5 | ++++ |

[a]Drug was administered IV at 80 mg/kg on day 3; 160 mg/kg on day 4; 240 mg/kg on day 5; and 120 mg/kg/injection BID on days 7–9.

[b]Drug was administered IV at 40 mg/kg on day 3; 80 mg/kg on day 4; and 160 mg/kg/injection QD on days 5–9.

[c]Drug was administered IV at 20 mg/kg on day 3; 40 mg/kg on day 4; and 106 mg/kg/injection QD on days 5–6.

TABLE III

EARLY STAGE MURINE MAMMARY ADENOCARCINOMA-16/C
(C3H female mice, CRL-Kingston)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 14 | ACTIVITY RATING |
|---|---|---|---|---|---|---|---|
| 0 | +0.0% | 0/5 | — | — | — | 0/5 | − |
| DILUENT INFUSION | +10.8 | 0/4 | 60% | 0.7 | 0.22 | 0/4 | − |
| 560[a] | DEATH | 5/5 | — | DEATH | — | 0/5 | DEATH |
| 560[b] | +10.9% | 0/4 | 37% | 2.0 | 0.6 | 0/4 | + |
| 680[c] | +7.6% | 0/5 | 39% | 2.5 | 0.75 | 0/5 | + |

[a]Drag was administered at 560 mg/kg by IV infusion over 3 hours on day 3.
[b]Drug was administered at 280 mg/kg/by IV infusion on days 3 and 7.
[c]Drug was administered IV at 80 mg/kg/injection on days 3–6; 120 mg/kg/injection on days 7–9.

TABLE IV

EARLY STAGE HUMAN COLON ADENOCARCINOMA-HCT116
(Balb/C SCID female mice, NCI)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 115 | ACTIVITY RATING |
|---|---|---|---|---|---|---|---|
| 0 | −4.2% | — | — | — | — | 0/5 | − |
| 560[a] | −4.0% | 0/5 | 0% | 56 | 6.7 | 2/5 | ++++ |
| 280[b] | 0% | 0/5 | 0% | 28 | 3.4 | 2/5 | ++++ |

[a]Drug was administered 140 mg/kg/injection IV on days 3, 4, 5, and 9.
[b]Drug was administered 70 mg/kg/injection IV on days 3, 4, 5, and 9.

TABLE V

EARLY STAGE TAXOL SENSITIVE HUMAN COLON ADENOCARCINOMA #15/0
(Balb/C SCID female mice, NCI)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 151 | ACTIVITY RATING |
|---|---|---|---|---|---|---|---|
| 0 | +4.3% | 0/5 | — | — | — | 0/5 | − |
| 420[a] | 0% | 0/5 | 0% | 33.5 | 5.0 | 1/5 | ++++ |

[a]Drug was administered 140 mg/kg/injection IV on days 3, 5, and 7.

TABLE VI

EARLY STAGE MURINE SQUAMOUS LUNG LC-12
(Balb/C female mice, NCI-Kingston)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 174 | ACTIVITY RATING |
|---|---|---|---|---|---|---|---|
| 0 | +6.5% | 0/5 | — | — | — | 0/5 | − |
| 640[a] | 0% | 0/4 | 14% | 12.5 | 1.7 | 0/4 | ++ |
| 1391[b] | +1.6% | 0/5 | 20% | 15.5 | 2.1 | 0/5 | +++ |

[a]Drug was administered at 160 mg/kg/injection IV on days 4, 6, 8, and 10.
[b]Drug was administered at 107 mg/kg/injection IV on days 4, 6, 8, 10, 12, 14, 16, 18, 20, 22, 24, 26, and 28.

TABLE VII

EARLY STAGE HUMAN PROSTATE LNCaP
(Balb/C SCID female mice, NCI)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 185 | ACTIVITY RATING |
|---|---|---|---|---|---|---|---|
| 0 | +3.9% | — | — | — | — | 0/5 | — |
| 840[a] | +5.6% | 0/5 | 0 | 60[b] | 7.2[b] | 4/5 | ++++ |

[a]Drug was administered at 140 mg/kg/injection IV on days 3, 5, 7, 9, 10, and 11.
[b]One mouse.

TABLE VIII

UPSTAGED HUMAN BREAST WSU-Br-1
(Balb/C SCID female mice, NCI)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 179 | ACTIVITY RATING |
|---|---|---|---|---|---|---|---|
| 0 | +3.9% | — | — | — | — | 0/5 | — |
| 725[a] | +3.9% | 0/5 | 0% | 57 | 2.9 | 2/5 | ++++ |
| 500[b] | +14% | 0/5 | 0% | 39 | 2.0 | 2/5 | ++++ |

[a]Drug was administered at 145 mg/kg/injection IV on days 11–13 and 19–20.
[b]Drug was administered at 100 mg/kg/injection IV on days 11–13 and 19–20.

TABLE IX

EARLY STAGE HUMAN OVARIAN BG-1
(Balb/C SCID female mice, NCI)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 176 | ACTIVITY RATING |
|---|---|---|---|---|---|---|---|
| 0 | 0% | — | — | — | — | 0/5 | — |
| 870[a] | −2.0% | 0/5 | 0% | 30.5 | 3.7 | 1/5 | ++++ |
| 600[b] | −3.0% | 0/5 | 0% | 30 | 3.6 | 0/5 | ++++ |

[a]Drug was administered at 145 mg/kg/injection IV on days 3–5 and 9–11.
[b]Drug was administered at 100 mg/kg/injection IV on days 3–5 and 9–11.

TABLE X

EARLY STAGE MURINE COLON CARCINOMA-26
((Balb/C female mice, NCI-Kingston-CRL)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 31 | ACTIVITY RATING |
|---|---|---|---|---|---|---|---|
| 0 | +1.8% | 0/5 | — | — | — | 0/5 | — |
| 1600[a] | +15% | 0/5 | 34% | 15 | 2.2 | 0/5 | +++ |
| 1305[b] | +15% | 0/5 | 28% | 6 | 0.9 | 0/5 | + |
| 1740[c] | +17% | 0/5 | 34% | 14 | 2.1 | 0/5 | +++ |

[a]Drug was administered at 100 mg/kg/injection IV BID on days 1, 3, 5, 7, 13, 15, 17, and 21.
[b]Drug was administered at 145 mg/kg/injection IV on days 1, 3, 5, 7, 9, 13, 15, 17, and 19.
[c]Drug was administered at 145 mg/kg/injection IV on days 1, 2, 3, 7, 8, 13, 14, 16, 18, and 20–22.

TABLE XI

EARLY STAGE HUMAN SQUAMOUS CELL LUNG CARCINOMA MRI-H165
(Balb/C SCID female mice, NCI)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 55 | ACTIVITY RATING |
|---|---|---|---|---|---|---|---|
| 0 | 0% | — | — | — | — | 0/5 | — |
| 600[a] | −2.1% | 0/5 | 0% | 31 | 3.7 | 0/5 | ++++ |

[a]Drug was administered at 100 mg/kg/injection IV on days 3–5 and 10–12.

TABLE XII

EARLY STAGE TAXOL RESISTANT HUMAN COLON ADENOCARCINOMA #15/MDR
(Balb/C SCID female mice, NCI)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 38 | ACTIVITY RATING |
|---|---|---|---|---|---|---|---|
| 0 | 0% | 0/5 | — | — | — | 0/5 | – |
| 500[a] | +2.1% | 0/5 | 10% | 11 | 1.4 | 0/5 | ++ |

[a]Drug was administered at 100 mg/kg/injection IV on days 3–5 and 13–14.

TABLE XIII

EARLY UPSTAGED MURINE COLON ADENOCARCINOMA-38 BY IV, PO, SC, AND IP ROUTES
(BDF1 female mice, CRL-Raleigh-NCI)

| TOTAL DOSE (mg/kg) | % BODY WT LOSS AT NADIR | DRUG DEATHS | % T/C MASS | GROWTH DELAY (DAYS) | LOG KILL | TUMOR FREE AT DAY 161 | ACTIVITY RATING |
|---|---|---|---|---|---|---|---|
| 0 | +6.5% | — | — | — | — | 0/5 | – |
| 450 IV[a] | +8.9% | 0/5 | 0% | 18 | 2.4[f] | 2/5 | ++++ |
| 780 PO[b] | +9.7% | 0/3 | 0% | All cures | >4.5 | 3/3 | ++++ |
| 450 PO[c] | +6.8% | 0/3 | 0% | 22.5 | 3.0[f] | 2/3 | ++++ |
| 450 SC[d] | +13.2% | 0/2 | 5.7% | 10.5 | 1.4[f] | 1/2 | ++/++++[g] |
| 450 IP[e] | +8.3% | 0/2 | 3.7% | 17 | 2.2[f] | 1/2 | +++/++++[g] |

[a]Drug was administered at 150 mg/kg/injection IV on days 5, 7, and 9.
[b]Drug was administered at 260 mg/kg/injection orally on days 5, 7, and 9.
[c]Drug was administered at 150 mg/kg/injection orally on days 5, 7, and 9.
[d]Drug was administered at 150 mg/kg/injection subcutaneously on days 5, 7, and 9.
[e]Drug was administered at 150 mg/kg/injection IP on days 5, 7, and 9.
[f]Log kill of regrowing tumors only (median).
[g]Activity rating for each mouse in study. One mouse was cured in each study, representing a "++++" rating. The other activity rating is based on the log kill calculated for the other mouse in the study.

We claim:
1. A compound of Formula I:

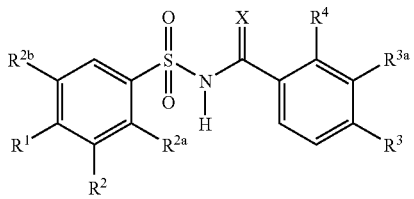

I where:
X is O;
$R^1$ is hydrogen, halo, $C_1$–$C_6$ alkyl, $C_1$–$C_4$ alkoxy, $C_1$–$C_4$ alkylthio, $CF_3$, $OCF_3$, $SCF_3$, ($C_1$–$C_4$ alkoxy)carbonyl, nitro, azido, $O(SO_2)CH_3$, $N(CH_3)_2$, hydroxy, phenyl, substituted phenyl, pyridinyl, thienyl, furyl, quinolinyl, or triazolyl;
$R^2$ is hydrogen, halo, cyano, $CF_3$, $C_1$–$C_6$ alkyl, ($C_1$–$C_4$ alkoxy)carbonyl, $C_1$–$C_4$ alkoxy, phenyl, or quinolinyl;
$R^{2a}$ is hydrogen or $C_1$–$C_4$ alkoxy;
$R^{2b}$ is hydrogen or $C_1$–$C_6$ alkyl provided that at least one of $R^{2a}$ and $R^{2b}$ is hydrogen;
$R^3$ is hydrogen, halo, $C_1$–$C_6$ alkyl, $CF_3$, or nitro;
$R^{3a}$ is hydrogen, halo, or $C_1$–$C_6$ alkyl provided that when $R^{3a}$ is $C_1$–$C_6$ alkyl, $R^3$ is hydrogen and $R^4$ is halo; and
$R^4$ is halo, $C_1$–$C_6$ alkyl, or $CF^3$ provided that only one of $R^3$ and $R^4$ may be $C_1$–$C_6$ alkyl and provided that when $R^4$ is halo or $C_1$–$C_6$ alkyl only one of $R^3$ and $R^{3a}$ is hydrogen; or a pharmaceutically acceptable base addition salt thereof, provided that:
a) when $R^3$ and $R^4$ are both chloro and $R^2$ is hydrogen, $R^1$ is bromo, iodo, $C_1$–$C_4$ alkoxy, $C_1$–$C_4$ alkylthio, $CF_3$, $OCF_3$, nitro, azido, $O(SO_2)CH_3$, $N(CH_3)_2$, hydroxy, phenyl, substituted phenyl, pyridinyl, thienyl, furyl, or triazolyl;
b) when $R^3$ and $R^4$ are both chloro and $R^1$ is hydrogen, $R^2$ is bromo, fluoro, $CF_3$, $C_1$–$C_6$ alkyl, $C_1$–$C_4$ alkoxy, phenyl, or quinolinyl.

2. The compound of claim 1, wherein $R^2$, $R^{2a}$, and $R^{2b}$ are hydrogen and $R^1$ is selected from the group consisting of hydrogen, halo, $C_1$–$C_6$ alkyl, $C_1$–$C_4$ alkoxy, $C_1$–$C_4$ alkylthio, $CF_3$, $OCF_3$, $SCF_3$, ($C_1$–$C_4$ alkoxy)carbonyl, nitro, azido, $O(SO_2)CH_3$, $N(CH_3)_2$, hydroxy, phenyl, substituted phenyl, pyridinyl, thienyl, furyl, quinolinyl, and triazolyl.

3. The compound of claim 1, wherein the compound is a pharmaceutically acceptable base addition salt.

4. The compound of claim 3, wherein the pharmaceutically acceptable base addition salt is a sodium salt.

5. The compound of claim 1 which is N-[2-chloro-4-bromobenzoyl]-4-chlorophenylsulfonamide or a base addition salt therof.

6. The compound of claim 1 which N-[2-methyl-4-chlorobenzoyl]-4-chlorophenylsulfonamide or a base addition salt thereof.

7. The compound of claim 5, wherein the base addition salt is a sodium salt.

8. A method of treating adenocarcinomas of the colon in a mammal comprising administering to a mammal in need of such treatment an oncolytically effective amount of a compound of Formula II:

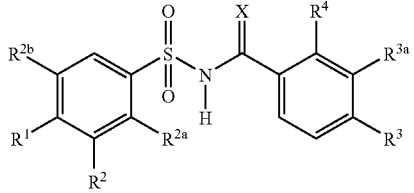

where:

X is O;

$R^1$ is hydrogen, halo, $C_1$–$C_6$ alkyl, $C_1$–$C_4$ alkoxy, $C_1$–$C_4$ alkylthio, $CF_3$, $OCF_3$, $SCF_3$, ($C_1$–$C_4$ alkoxy)carbonyl, nitro, azido, $O(SO_2)CH_3$, $N(CH_3)_2$, hydroxy, phenyl, substituted phenyl, pyridinyl, thienyl, furyl, quinolinyl, or triazolyl;

$R^2$ is hydrogen, halo, cyano, $CF_3$, $C_1$–$C_6$ alkyl, ($C_1$–$C_4$ alkoxy)carbonyl, $C_1$–$C_4$ alkoxy, phenyl, or quinolinyl;

$R^{2a}$ is hydrogen or $C_1$–$C_4$ alkoxy;

$R^{2b}$ is hydrogen or $C_1$–$C_6$ alkyl provided that at least one of $R^{2a}$, and $R^{2b}$ is hydrogen;

$R^3$ is hydrogen, halo, $C_1$–$C_6$ alkyl, $CF_3$, or nitro;

$R^{3a}$ is hydrogen, halo, or $C_1$–$C_6$ alkyl provided that when $R^{3a}$ is $C_1$–$C_6$ alkyl, $R^3$ is hydrogen and $R^4$ is halo; and $R^4$ is halo, $C_1$–$C_6$ alkyl, or $CF_3$ provided that only one of $R^3$ and $R^4$ may be $C_1$–$C_6$ alkyl and provided that when $R^4$ is halo or $C_1$–$C_6$ alkyl only one of $R^3$ and $R^{3a}$ is hydrogen; or a pharmaceutically acceptable base addition salt thereof.

9. A pharmaceutical formulation comprising a compound of Formula II:

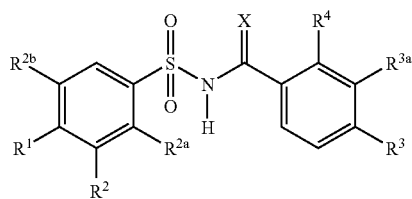

where:

X is O;

$R^1$ is hydrogen, halo, $C_1$–$C_6$ alkyl, $C_1$–$C_4$ alkoxy, $C_1$–$C_4$ alkylthio, $CF_3$, $OCF_3$, $SCF_3$, ($C_1$–$C_4$ alkoxy)carbonyl, nitro, azido, $O(SO_2)CH_3$, $N(CH_3)_2$, hydroxy, phenyl, substituted phenyl, pyridinyl, thienyl, furyl, quinolinyl, or triazolyl;

$R^2$ is hydrogen, halo, cyano, $CF_3$, $C_1$–$C_6$ alkyl, ($C_1$–$C_4$ alkoxy)carbonyl, $C_1$–$C_4$ alkoxy, phenyl, or quinolinyl;

$R^{2a}$ is hydrogen or $C_1$–$C_4$ alkoxy;

$R^{2b}$ is hydrogen or $C_1$–$C_6$ alkyl provided that at least one of $R^{2a}$ and $R^{2b}$ is hydrogen;

$R^3$ is hydrogen, halo, $C_1$–$C_6$ alkyl, $CF_3$, or nitro;

$R^{3a}$ is hydrogen, halo, or $C_1$–$C_6$ alkyl provided that when $R^{3a}$ is $C_1$–$C_6$ alkyl, $R^3$ is hydrogen and $R^4$ is halo; and $R^4$ is halo, $C_1$–$C_6$ alkyl, or $CF_3$ provided that only one of $R^3$ and $R^4$ may be $C_1$–$C_6$ alkyl and provided that when $R^4$ is halo or $C_1$–$C_6$ alkyl only one of $R^3$ and $R^{3a}$ is hydrogen; or a pharmaceutically acceptable base addition salt thereof, and a pharmaceutically acceptable carrier, diluent, or excipient.

10. The compound of claim 2, wherein the compound is a pharmaceutically acceptable base addition salt.

11. The compound of claim 6, wherein the base addition salt is a sodium salt.

* * * * *

UNITED STATES PATENT AND TRADEMARK OFFICE
CERTIFICATE OF CORRECTION

PATENT NO. : 7,183,320 B2 Page 1 of 1
APPLICATION NO. : 10/478389
DATED : February 27, 2007
INVENTOR(S) : Chuan Shih et al.

It is certified that error appears in the above-identified patent and that said Letters Patent is hereby corrected as shown below:

Title Page,
Insert Item [60]
-- (60) Related U.S. Application Data
 Provisional application 60/296,350, June 6, 2001

Signed and Sealed this

Third Day of August, 2010

David J. Kappos
*Director of the United States Patent and Trademark Office*